(12) United States Patent
Famodu et al.

(10) Patent No.: US 6,512,164 B1
(45) Date of Patent: Jan. 28, 2003

(54) THIAMINE BIOSYNTHETIC ENZYMES

(75) Inventors: Omolayo O. Famodu, Newark, DE (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 31 days.

(21) Appl. No.: 09/594,506

(22) Filed: Jun. 15, 2000

Related U.S. Application Data

(60) Provisional application No. 60/139,556, filed on Jun. 16, 1999.

(51) Int. Cl.$^7$ .......................... A01H 1/00; C07H 21/04; C07K 14/415; C12N 5/14; C12N 9/00

(52) U.S. Cl. .......................... 800/278; 435/6; 435/69.1; 435/183; 435/410; 435/419; 435/252.3; 435/320.1; 530/370; 536/23.1; 536/23.2; 536/23.6; 536/24.1; 536/24.3; 536/24.33; 800/295

(58) Field of Search .......................... 435/6, 69.1, 183, 435/410, 419, 252.3, 320.1; 530/370; 536/23.1, 23.2, 23.6, 24.1, 24.3, 24.33; 800/278, 295

(56) References Cited

PUBLICATIONS

Vander Horn et al., J. Bacteriol., vol. 175, Oct. 1, 1993, pp. 982–992, Structural Genes for Thiamine Biosynthetic Enzymes (thiCEFGH) in *Escherichia coli* K–12.
Zhang et al., J. Bacteriol., vol. 179, Oct. 1, 1997, pp. 3030–3035, Characterization of the *Bacillus subtilis* thiC Operon Involved in Thiamine Biosynthesis.
Carlos R. Machado et al., J. Mol. Biol., vol. 273, 1997, pp. 114–121, Dual Role for the Yeast TH14 Gene in Thiamine Biosynthesis and DNA Damage Tolerance.
Belanger et al., Plant Mol. Biol., vol. 29, Oct. 1, 1995, pp. 809–821, Evidence for the Thiamine Biosynthetic Pathway in Higher–Plant Plastids and Its Developmental Regulation.
National Center for Biotechnology Information General Identifier No.:2501189, Jul. 15, 1999.
National Center for Biotechnology Information General Identifier No. 2501190, Jul. 15, 1999.
National Center for Biotechnology Information General Identifier No. 6552395, Dec. 10, 1999.
National Center for Biotechnology Information General Identifier No. 6094476, Jul. 15, 1999.
Debora Jacob–Wilk et al., Plant Mol. Biol., vol. 35:661–666, 1997, Induction of a Citrus Gene Highly Homologous to Plant and Yeast THI Genes Involved in Thiamine Biosynthesis During Natural and Ethylene Induced Fruit Maturation.
National Center for Biotechnology Information General Identifier No. 3041750, May 30, 2000.
N. J. Cummings et al., Microbiology, vol. 143:1855–1859, 1997, The *Bacillus subtilis* 168 Chromosome from SSPE to KATA.
National Center for Biotechnology Information General Identifier No. 421172, Jun. 30, 1995.
National Center for Biotechnology Information General Identifier No. 417994, May 30, 2000.
Frederick R. Blattner et al., Nucl. Acids Res., vol. 21(23):5408–5417, Analysis of the *Escherichia coli* Genome, IV. DNA Sequence of the Regions from 89.2 to 92.8 Minutes.
National Center for Biotechnology Information General Identifier No. 3024726, May 30, 2000.
S. T. Cole et al., Nature, vol. 393:537–544, Jun. 11, 1998, Deciphering the Biology of *Mycobacterium tuberculosis* from the Commplete Genome Sequence.
National Center for Biotechnology Information General Identifier No. 3582335, Apr. 5, 2000.
Xiaoying Lin et al., Nature, vol. 402:761–768, Dec. 16, 1999, Sequence and Analysis of Chromosome 2 of the Plant *Arabidopsis thaliana*.

*Primary Examiner*—Phuong T. Bui

(57) ABSTRACT

This invention relates to an isolated nucleic acid fragment encoding a thiamine biosynthetic enzyme. The invention also relates to the construction of a chimeric gene encoding all or a substantial portion of the thiamine biosynthetic enzyme, in sense or antisense orientation, wherein expression of the chimeric gene results in production of altered levels of the thiamine biosynthetic enzyme in a transformed host cell.

14 Claims, 6 Drawing Sheets

```
SEQ ID NO:39    MAT--AAA-------------SSLLKSSFAGSRLPAATRTTPASLVVATGPRGAGAGPICASMS
SEQ ID NO:40    MAT--TAA-------------SSLLKSSFAGSRLPSATRTTPSSVAVATPR-AGGGPI--RAS
SEQ ID NO:22    MAAMATTA-------------SSLLKTSFAGARLPAAARNPT-----VSVAPRT--GGAICNSIS
SEQ ID NO:24    MAAMATTTLSSNP------KL--SFFHGKPVTYSSRVAPTTKLFSSKQ------GTISMSLT
SEQ ID NO:26    MAAMATTA--------------SSLLKPSFSGVRLPAAARTPS-----CVATPRA--G-AICNSIS
SEQ ID NO:30    ---------------------------------------HEATRTPS-----CAATRRT---GAICNSIS
                                                                             60
                   ******                              *  *   *  * ***********

SEQ ID NO:39    MSSSNPPYDLTSFRFSPIKESIVSREMTRRYMTDMITYADTDVVIVGAGSAGLSCAYELS
SEQ ID NO:40    ISSPNPPYDLTSFRFSPIKESIVSREMTRRYMTDMITHADTDVVIVGAGSAGLSCAYELS
SEQ ID NO:22    SSSSTPPYDLNAIRFSPIKESIVSREMTRRYMTDMITYADTDVVVGAGSAGLSCAYELS
SEQ ID NO:24    Q-----PPYDLQSFKFQPIKESIVSREMTRRYMTDMITYADTDVVIVGAGSAGLSCAYEIS
SEQ ID NO:26    SS---TPPYDLNAFKFSPIKESIVSREMTRRYMTDMITYADTDVVIVGAGSAGLSCAYELS
SEQ ID NO:30    ---SCTPPYDLSSFKFSPMKESVASREMIRRYMTDMIADVNTDVIIIGTGSAGLSCAYELS
                                                                            120
                 *  *           ****    ***  *  **********  *** *************

SEQ ID NO:39    KDPAVSIAIVEQSVSPGGGAWLGGQLFSAMVVRKPAHLFLDELGVAYDEAEDYVVIKHAA
SEQ ID NO:40    KDPTVSVAIVEQSVSPGGGAWLGGQLFSAMVVRRPAHLFLDELGVYDEAEDYVVVKHAA
SEQ ID NO:22    KDPSVSVSVAVIEQSVSPGGGAWLGGQLFSAMVVRKPAHLFLDELGVAYDEQEDYVVIKHAA
SEQ ID NO:24    KNPAVSVAIIEQSVSPGGAWLGGQLFSAMVVRKPAHLFLDELGVAYDEQEDYVVIKHAA
SEQ ID NO:26    KDPSISIAIIEQSVSPGGGAWLGGQLFSAMVVRKPAHLFLDELNIEYDEQEDYVVIKHAA
SEQ ID NO:30    KDPSVNIAIIQRSVSPGGSGWLGSQLFSAMVVRKPAHLFLDELNIEYDEQEDYVVIKHAA
                                                                            180
                 *  *   *  ****       ***  ********  ****** ***  *  ***********
```

FIG. 1A

```
                    *******   * ******************   **   ***      *  **
SEQ ID NO:39    LFTSTVMSLLLARPNVKLFNAVAVEDLIVRGGRVGGVVTNWALVSMNHDT-----QSCMDP
SEQ ID NO:40    LFTSTVMSRLLARPNVKLFNAVAVEDLIVRRGRVGGVVTNWALVSMNHDT-----QSCMDP
SEQ ID NO:22    LFTSTVMSRLLARPNVKLFNAVAVEDLIVKEGRVGGVVTNWALVSMNHDT-----QSCMDP
SEQ ID NO:24    LFTSTIMSRLLARPNVKLFNAVAAEDLIVKEGRVAGVVTNWALVSMNHDT-----QSCMDP
SEQ ID NO:26    LFTSTVMSRLLARPNVKLFNAVAVEDLIVKEDRVAGVVTNWALVSMNHDT-----QSCMDP
SEQ ID NO:30    LFTSTVLSRLLARPNVKLFNGVVVEDLVVKEHRVTGVVTNWALVSMNQDTHSQTQSHMDA
                                                                          240

****   **********    * ****   ****  *     *  ***********
SEQ ID NO:39    NVMEAKVVVSSCGHDGPFGATG--VKRLQDIGMISAVP--GMKALDMNTAEDEIVRLTRE
SEQ ID NO:40    NVMEAKVVVSSCGHDGPFGATG--VKRLQDIGMISAVP--GMKALDMNAAEDEIVRLTRE
SEQ ID NO:22    NVMESRVVVSSCGHDGPFGATG--VKRLQDIGMIDAVP--GMRALDMNTAEDEIVRLTRE
SEQ ID NO:24    NVMEAKVVVSSCGHDGPFGATG--VKRLKSIGMIDSVP--GMKALDMNAAEDAIVRLTRE
SEQ ID NO:26    NVMEAKVVVSSCGHDGPFGATG--VKRLQDIGMIQAVP--GMKALDMNTAEDAIVRLTRE
SEQ ID NO:30    NVMEAKIVVSSCGHEGLFSANGKGVKRLEDIGMIKTVPRTGMEALDTNVSEDAIVGLTRE
                241                                                       300

*******  * ****** ***   ****  ****************   *
SEQ ID NO:39    VVPGMIVTGMEVAEIDGAPRMGPTFGAMMISGQKAAHLALKALGRPNAVDGTM---SPPL
SEQ ID NO:40    VVPGMIVTGMEVAEIDGAPRMGPTFGAMMISGQKAAHLALKALGRPNAVDGTIPEVSPAL
SEQ ID NO:22    VVPGMIVTGMEVAEIDGAPRMGPTFGAMMISGQKAAHLALKALGRPNAIDGTIKKAAAAA
SEQ ID NO:24    IVPGMIVTGMEVAEIDGSPRMGPTFGAMMISGQKAAHLALKALGRNNAIDGT---CGVGR
SEQ ID NO:26    VVPGMIVTGMEVAEIDGAPRMGPTFGAMMISGQKAAHLALKALGRPNGIDGTLKNVTPAL
SEQ ID NO:30    VVPGMIVAGIEVAEIDGPQRMCPTFGATIISGQKAAHLALKALGRPNGIDS---------
                301                                                       360
```

FIG. 1B

```
SEQ ID NO:39   -REELMIAYKDD-EVVDA
SEQ ID NO:40   -REEFVIASKDD-EVVDA
SEQ ID NO:22   AHPELILASKDDGEIVDA
SEQ ID NO:24   EEPQLIFASADTEEIVDA
SEQ ID NO:26   -HPEMILAATNNGDIVDA
SEQ ID NO:30   -----------------ETVPA
               361              378
```

FIG. 1C

```
SEQ ID NO:41    MQNN----------------------------------------------------------
SEQ ID NO:32    --------------------------------------------------------------
SEQ ID NO:38    --------------------------------------------------------------
SEQ ID NO:42    MAASVHCTLMSVVCNNKNHSARPKLPNSSLLPGFDVVVQAAATRFKKETTTRATLTFDP
                1                                                           60

*+*+*++++
SEQ ID NO:41    TTGSFGEEENA--------------PVRVYDTSGPYTDPEVTINIQEG----LK-PLRQIWI
SEQ ID NO:32    -----------------------------------------------------TRPVLKVPFRRVHL
SEQ ID NO:38    ----------HETKHTVDPAAPEFLPLPAFEDCFPRSTKECSEVVHEETGHALKVPFRRVHL
SEQ ID NO:42    PTTNSERAKQRKHTIDPSSPDFQPIPSFEECFPKSTKEHKEVVHEESGHVLKVPFRRVHL
                61                                                         120

**   ++   +++++*+++         ++  + +++++++++++++++  +++++*+++++*
SEQ ID NO:41    TERGDVEEYEGRAIKPEDNGYKKAKPNVSYPGLKRKPLRAK---AGQNVTQMHYAKKGII
SEQ ID NO:32    T--GDQKHFD----TYDTSGPQNISPRIGLPKIRKEWIDRREKLGSPRYTQMYYAKQGIV
SEQ ID NO:38    T--GDSGHFD----TYDTSGPQNISPRLGLPKIRKEWIDRREKLGSPRYTQMYYAKQGII
SEQ ID NO:42    S--GGEPAFD----NYDTSGPQNVNAHIGLAKLRKEWIDRREKLGTPRYTQMYYAKQGII
                121                                                        180

*+*  ++++  **   ***  ***+***+************+* *+*+*+*****+**+ *+*+***+*******
SEQ ID NO:41    TPEMEFIAIREHVSPEFVRDEVASGRAIIPSNINHPESEPMIIGRNFHVKINANIGNSAV
SEQ ID NO:32    TEEMLYCASRENLSPEFVRTEVARGRAIIPSNKRHLELEPMIVGRNFLVKVNANIGNSAV
SEQ ID NO:38    TEEILYCAKRENLAPEFVRSEVARGRAIIPSNKRHLELEPMIVGRNFLVKVNANIGNSAV
SEQ ID NO:42    TEEMLYCATREKLDPEFVRSEVARGRAIIPSNKKHLELEPMIVGRKFLVKVNANIGNSAV
                181                                                        240
```

FIG. 2A

```
                    ********** + +*****+*   *** **  *  ** *****************
SEQ ID NO:41        TSSIEEEVERKMTWAIRWGADTMDLSTGKDIHTTREWIIRNCPVPVGTVPIYQALEKVNG
SEQ ID NO:32        VSSIEEEVHKLQWATMWGADTVMDLSTGRHIHETREWIIRNSPVPIGTVPIYQALEKVNG
SEQ ID NO:38        VSSIEEEVHKLQWATMWGADTVMDLSTGRHIHETREWIIRNSSVPIGTVPIYQALEKVNG
SEQ ID NO:42        ASSIEEEVYKVQWATMWGADTIMDLSTGRHIHETREWILRNSAVPVGTVPIYQALEKVDG
                    241                                                       300

+*** *  *** +*  ********************+++**  ***** +++++++*
SEQ ID NO:41        VAEDLTWEIYRDTLIEQAEQGVDYFTIHAGVLLRYVPLTAKRTTGIVSRGGAIMAQWCLA
SEQ ID NO:32        IAENLSWEIFRDTLIEQAEQGVDYFTIHAGVLLRYIPLTAKRMTGIVSRGGSIHAKWCLT
SEQ ID NO:38        IAEDLSWEVFRDTLIEQAEQGVDYFTIHAGVLLRYIPLTAKRMTGIVSRGGSIHAKWCLT
SEQ ID NO:42        IAENLNWEVFRETLIEQAEQGVDYFTIHAGVLLRYIPLTAKRLTGIVSRGGSIHAKWCLA
                    301                                                       360

+*+*+*+*+++*+*+ ***********************  ***** ****+++++
SEQ ID NO:41        HHQESFLYTHFEEICEIMKMYDIAFSLGDGLRPGSIADANDEAQFAELETLGELTQIAWK
SEQ ID NO:32        YHKENFAYEHWDDILDICNQYDVALSIGDGLRPGSIYDANDSAQFAELLTQGELTRRAWA
SEQ ID NO:38        YHKENFAYEHWDDILDICNQYDVALSIGDGLRPGSIYDANDSAQFAELLTQGELTRRAWE
SEQ ID NO:42        YHKENFAYEHWDDILDICNQYDVALSIGDGLRPGSIYDANDTAQFAELLTQGELTRRAWE
                    361                                                       420

+*+*+*+++++*+   *  +  **********************************+
SEQ ID NO:41        HDVQVMIEGPGHVPMHKIKENVDKQMDICKEAPFYTLGPLTTDIAPGYDHITSAIGAAMI
SEQ ID NO:32        KDVQVMNEGPGHIPMHKIPENMEKQLEWCNEAPFYTLGPLTTDIAPGYDHITSAIGAANI
SEQ ID NO:38        KDVQVMNEGPGHIPMHKIPENMEKQLEWCNEAPFYTLGPLTTDIAPGYDHITSAIGAANI
SEQ ID NO:42        KDVQVMNEGPGHVPMHKIPENMQKQLEWCNEAPFYTLGPLTTDIAPGYDHITSAIGAANI
                    421                                                       480
```

FIG. 2B

```
                      *+*+*+*+*         ***************+********    ***   *** ** *+*+***********
SEQ ID NO:41     GWYGTAMLCYVTPKEHLGLPNRDDVREGVITYKIAAHAADLAKGHPGAQIRDDALSKARF
SEQ ID NO:32     GALGTALLCYVTPKEHLGLPNRDDVKTGVISYKISAHAADLAKGHPYAQAWDDALSKARF
SEQ ID NO:38     GALGTALLCYVTPKEHLGLPNRDDVKTGVISYKIAAHAADLAKRHPYAQAWDDALSKARF
SEQ ID NO:42     GALGTALLCYVTPKEHLGLPNRDDVKAGVIAYKIAAHAADLAKQHPHAQAWDDALSKARF
                 481                                                        540

****  ****+******   +++ +********    ******************+++++*+*+***  +  +
SEQ ID NO:41     EFRWRDQFNLSLDPERALEYHDETLPAEGAKTAHFCSMCGPKFCSMRISQDIRDYAKKND
SEQ ID NO:32     EFRWLDQFALSLDPVTAMAFHDETLPSEGAKVAHFCSMCGPKFCSMKITEDIRKYADENG
SEQ ID NO:38     EFRWLDQFALSLDPVTAMSFHDETLPSDGAKVAHFCSMCGPKFCSMKITEDIRKYADEHG
SEQ ID NO:42     EFRWMDQFALSLDPMTAMSFHDETLPADGAKVAHFCSMCGPKFCSMKITEDIRKYAEENG
                 541                                                        600

++   *  +*+   +++  ** *   +  +++++++++++  *+++* ++++
SEQ ID NO:41     LSEAE-AINKGLKEKAKEFV------------DTGSNLY--------Q-------
SEQ ID NO:32     YGTVEEAVIQGMNAMSAEFLAARKTISGEQHGEAGGEIYVPESYAAQK-------
SEQ ID NO:38     YGTVEEAVRQGMSEMSAEFLAARKTISGEQHGEAGGEIYVPESYVVQK-------
SEQ ID NO:42     YGSAEEAIRQGMDAMSEEFNIAKKTISGEQHGEVGGEIYLPESYVKAAQK
                 601                                              650
```

FIG. 2C

SEQUENCE LISTING

<160> NUMBER OF SEQ ID NOS: 45

<210> SEQ ID NO 1
<211> LENGTH: 571
<212> TYPE: DNA
<213> ORGANISM: Oryza sativa
<220> FEATURE:
<221> NAME/KEY: unsure
<222> LOCATION: (392)
<221> NAME/KEY: unsure
<222> LOCATION: (534)
<221> NAME/KEY: unsure
<222> LOCATION: (548)
<221> NAME/KEY: unsure
<222> LOCATION: (557)
<221> NAME/KEY: unsure
<222> LOCATION: (568)

<400> SEQUENCE: 1
gtttaaacca gagcaagaag ctcagctcct cctcctctcg catggcagcc atggccacca      60
ccgcgtccag cctcctcaag acctccttcg ctggcgcgcg cctccccgcc gccgcccgca     120
accccaccgt ctccgtcgcg ccgcgcaccg gcggcgccat ctgcaactcc atctcgtcgt     180
cgtcgtccac tccccctac gacctcaacg ccatcaggtt cagccccatc aaggagtcca     240
tcgtgtctcg cgagatgacc cggcggtaca tgaccgacat gatcacctac gccgacaccg     300
acgtcgtcgt cgtcggcgcc ggctccgcgg ggctctcctg cgcgtacgag ctctccaagg     360 accctccgt cagcgtcgcc gtcatcgagc antcggtgtc cccggcggcg gcgcgtggct     420
cggcgggcag ctgttctccg ccatggtggt gcgcaagccg gcgcactgtt ctcgacgagc     480
tcgggtccgt agaagagcag gaggatacgt cgtcatcaag cacgcgggct cttnactcaa     540
cgtataancg ctctggngcg ccaacgtnaa t                                    571

<210> SEQ ID NO 2
<211> LENGTH: 105
<212> TYPE: PRT
<213> ORGANISM: Oryza sativa
<220> FEATURE:
<221> NAME/KEY: UNSURE
<222> LOCATION: (80)

<400> SEQUENCE: 2

Gly Ala Ile Cys Asn Ser Ile Ser Ser Ser Ser Thr Pro Pro Tyr
 1               5                  10                  15

Asp Leu Asn Ala Ile Arg Phe Ser Pro Ile Lys Glu Ser Ile Val Ser
             20                  25                  30

Arg Glu Met Thr Arg Arg Tyr Met Thr Asp Met Ile Thr Tyr Ala Asp
         35                  40                  45

Thr Asp Val Val Val Gly Ala Gly Ser Ala Gly Leu Ser Cys Ala
     50                  55                  60

Tyr Glu Leu Ser Lys Asp Pro Ser Val Ser Val Ala Val Ile Glu Xaa
 65                  70                  75                  80

Ser Val Ser Pro Gly Gly Gly Ala Trp Leu Gly Gly Gln Leu Phe Ser
                 85                  90                  95

Ala Met Val Val Arg Lys Pro Ala His
            100                 105

<210> SEQ ID NO 3
<211> LENGTH: 451
<212> TYPE: DNA

```
<213> ORGANISM: Glycine max
<220> FEATURE:
<221> NAME/KEY: unsure
<222> LOCATION: (27)

<400> SEQUENCE: 3
ccaaatatca tcatctgaaa cgatggntgc catggcaacc acaaccctct cttcaaaccc       60
gaaactctca tttttccacg gaaagcccgt tacatattct tcccgcgtcg cacccaccac      120
caagttattc tcatccaaac aaggcacaat ctccatgtcc ctaacccaac ccccatacga      180
cctccaatcc ttcaaattcc aacccatcaa agaatccatc gtctcacgcg aaatgacgcg      240
ccgctacatg accgacatga taacctacgc cgacaccgac gtcgtaatcg tcggagccgg      300
ctcggcgggg ctctcctgtg cgtacgagat cagcaagaac cccgccgtga gcgtcgccat      360
aatcgagcag tccgtgagcc ccggcggcgg cgcgtggctc ggcggacaac tcttctccgc      420
catggtgggt tcgcaagccg gcgcacctct t                                    451

<210> SEQ ID NO 4
<211> LENGTH: 101
<212> TYPE: PRT
<213> ORGANISM: Glycine max

<400> SEQUENCE: 4

Thr Ile Ser Met Ser Leu Thr Gln Pro Pro Tyr Asp Leu Gln Ser Phe
 1               5                  10                  15

Lys Phe Gln Pro Ile Lys Glu Ser Ile Val Ser Arg Glu Met Thr Arg
            20                  25                  30

Arg Tyr Met Thr Asp Met Ile Thr Tyr Ala Asp Thr Asp Val Val Ile
        35                  40                  45

Val Gly Ala Gly Ser Ala Gly Leu Ser Cys Ala Tyr Glu Ile Ser Lys
    50                  55                  60

Asn Pro Ala Val Ser Val Ala Ile Ile Glu Gln Ser Val Ser Pro Gly
65                  70                  75                  80

Gly Gly Ala Trp Leu Gly Gly Gln Leu Phe Ser Ala Met Val Val Arg
                85                  90                  95

Lys Pro Ala His Leu
            100

<210> SEQ ID NO 5
<211> LENGTH: 498
<212> TYPE: DNA
<213> ORGANISM: Triticum aestivum
<220> FEATURE:
<221> NAME/KEY: unsure
<222> LOCATION: (394)
<221> NAME/KEY: unsure
<222> LOCATION: (429)
<221> NAME/KEY: unsure
<222> LOCATION: (470)

<400> SEQUENCE: 5
cacagctcca cacaccatgg cagccatggc caccaccgcc tccagcctcc tcaagccctc       60
cttctccggc gtccgcctcc cggcggcggc ccgcaccccg tcctgcgtcg ccaccccgcg      120
tgccggcgcc atctgcaact ccatctcctc ctccacacct ccctacgacc tcaacgcctt      180
caagttcagc cccatcaagg agtccatcgt gtcccgcgag atgacccgcc gctacatgac      240
cgacatgatc acctacgccg acaccgacgt cgtcatcgtc ggcgcggat ccgcggggct      300 ttcctgcgcg tacgagctct ccaaggaccc ctccatcagc atcgccatca tcgagcagtc      360
```

```
cgtgtccccc ggcggcggcg cctggctcgg cggncagctc ttctccgcca tggtcgtgcg    420
caagccggng caactctcct cgacgagctc aacatcgagt acgacaacan gaggatactc    480
gtcatcaagc acccgcgc                                                  498
```

<210> SEQ ID NO 6
<211> LENGTH: 105
<212> TYPE: PRT
<213> ORGANISM: Triticum aestivum
<220> FEATURE:
<221> NAME/KEY: UNSURE
<222> LOCATION: (103)

<400> SEQUENCE: 6

```
Ala Gly Ala Ile Cys Asn Ser Ile Ser Ser Thr Pro Pro Tyr Asp
 1               5                  10                  15

Leu Asn Ala Phe Lys Phe Ser Pro Ile Lys Glu Ser Ile Val Ser Arg
                20                  25                  30

Glu Met Thr Arg Arg Tyr Met Thr Asp Met Ile Thr Tyr Ala Asp Thr
            35                  40                  45

Asp Val Val Ile Val Gly Ala Gly Ser Ala Gly Leu Ser Cys Ala Tyr
        50                  55                  60

Glu Leu Ser Lys Asp Pro Ser Ile Ser Ile Ala Ile Ile Glu Gln Ser
 65                 70                  75                  80

Val Ser Pro Gly Gly Gly Ala Trp Leu Gly Gly Gln Leu Phe Ser Ala
                85                  90                  95

Met Val Val Arg Lys Pro Xaa Gln Leu
            100                 105
```

<210> SEQ ID NO 7
<211> LENGTH: 464
<212> TYPE: DNA
<213> ORGANISM: Oryza sativa
<220> FEATURE:
<221> NAME/KEY: unsure
<222> LOCATION: (269)
<221> NAME/KEY: unsure
<222> LOCATION: (340)..(341)
<221> NAME/KEY: unsure
<222> LOCATION: (371)
<221> NAME/KEY: unsure
<222> LOCATION: (374)
<221> NAME/KEY: unsure
<222> LOCATION: (384)
<221> NAME/KEY: unsure
<222> LOCATION: (389)
<221> NAME/KEY: unsure
<222> LOCATION: (395)
<221> NAME/KEY: unsure
<222> LOCATION: (421)
<221> NAME/KEY: unsure
<222> LOCATION: (426)

<400> SEQUENCE: 7

```
tacacatgga gtccaggctg gtggtgagct cctgcggcca cgacgggccg ttcggcgcca     60
cgggcgtcaa gcggctgcag gacatcggca tgatcgacgc cgtgcccggc atgcgcgccc    120
tcgacatgaa caccgccgag gacgagatcg tccgcctcac ccgcgaggtc gtccccggca    180
tgatcgtcac cggcatggag gtcgccgaga tcgacgcgc cccgagaatg ggcccgacgt    240
tcggagccat gatgatctcc ggccagaang cggcgcacct ggcgctgaag gcgctcggcc    300
ggccgaacgc catcgacggc acgatcaaca aggcggcggn ngcggcggcg cacccggagc    360
tgatcctggc ntcnaaggac gacngcgant tcgtngaccc tgagcgaata gaacaaggta    420
```

-continued naaaanatcc gcaagactgg tggtgacacg gatgattggg gaca            464

<210> SEQ ID NO 8
<211> LENGTH: 126
<212> TYPE: PRT
<213> ORGANISM: Oryza sativa
<220> FEATURE:
<221> NAME/KEY: UNSURE
<222> LOCATION: (88)
<221> NAME/KEY: UNSURE
<222> LOCATION: (112)

<400> SEQUENCE: 8

Met Glu Ser Arg Val Val Ser Ser Cys Gly His Asp Gly Pro Phe
 1               5                  10                  15

Gly Ala Thr Gly Val Lys Arg Leu Gln Asp Ile Gly Met Ile Asp Ala
                20                  25                  30

Val Pro Gly Met Arg Ala Leu Asp Met Asn Thr Ala Glu Asp Glu Ile
            35                  40                  45

Val Arg Leu Thr Arg Glu Val Val Pro Gly Met Ile Val Thr Gly Met
    50                  55                  60

Glu Val Ala Glu Ile Asp Gly Ala Pro Arg Met Gly Pro Thr Phe Gly
65                  70                  75                  80

Ala Met Met Ile Ser Gly Gln Xaa Ala Ala His Leu Ala Leu Lys Ala
                85                  90                  95

Leu Gly Arg Pro Asn Ala Ile Asp Gly Thr Ile Asn Lys Ala Ala Xaa
            100                 105                 110

Ala Ala Ala His Pro Glu Leu Ile Leu Ala Ser Lys Asp Asp
        115                 120                 125

<210> SEQ ID NO 9
<211> LENGTH: 509
<212> TYPE: DNA
<213> ORGANISM: Glycine max
<220> FEATURE:
<221> NAME/KEY: unsure
<222> LOCATION: (333)
<221> NAME/KEY: unsure
<222> LOCATION: (363)
<221> NAME/KEY: unsure
<222> LOCATION: (378)
<221> NAME/KEY: unsure
<222> LOCATION: (386)..(387)
<221> NAME/KEY: unsure
<222> LOCATION: (399)
<221> NAME/KEY: unsure
<222> LOCATION: (401)
<221> NAME/KEY: unsure
<222> LOCATION: (414)
<221> NAME/KEY: unsure
<222> LOCATION: (431)
<221> NAME/KEY: unsure
<222> LOCATION: (446)
<221> NAME/KEY: unsure
<222> LOCATION: (462)
<221> NAME/KEY: unsure
<222> LOCATION: (476)
<221> NAME/KEY: unsure
<222> LOCATION: (484)
<221> NAME/KEY: unsure
<222> LOCATION: (503)

<400> SEQUENCE: 9
gaaaccaaaa ctgaaaaaaa aaacaaacaa taccataaca tggcttcttc caccatcacc       60
tcctccttcc taacatcacc cccttcatct ctcttcaaca aatcatcatc cccttccttc      120
catgccaccc ctactctccg cccccctcgcg ccacgcgcct ccatgtccgc ctcagcgccg      180

-continued

```
ccctacgact tcggatcgtt ccggttcgat ccgattagag agtcgattgt gtcgcgcgag      240
atgacccgca ggtacatgat cgacatggtc acccacgccg acaccgacgt cgtcatcgtt      300
ggcgcgggct ccgcgggtct ctcgtgcgcc tangagctct ccaaaaaccc ctccaacaac      360
atngccattg ttgagcantc cgtcannccc ggggggggng nctgggtcgg gggncaactc      420
tctcgcatgg nagtgggtta gcccgnacaa ctcttcctaa angagctcaa tgtgngtat       480 taanaaacaa aacaacttgt ggnggttaa                                        509
```

<210> SEQ ID NO 10
<211> LENGTH: 113
<212> TYPE: PRT
<213> ORGANISM: Glycine max
<220> FEATURE:
<221> NAME/KEY: UNSURE
<222> LOCATION: (84)
<221> NAME/KEY: UNSURE
<222> LOCATION: (94)
<221> NAME/KEY: UNSURE
<222> LOCATION: (99)
<221> NAME/KEY: UNSURE
<222> LOCATION: (102)
<221> NAME/KEY: UNSURE
<222> LOCATION: (107)

<400> SEQUENCE: 10

```
Pro Ser Ser Leu Phe Asn Lys Ser Ser Pro Ser Phe His Ala Thr
 1               5                  10                  15

Pro Thr Leu Arg Pro Leu Ala Pro Arg Ala Ser Met Ser Ala Ser Ala
                20                  25                  30

Pro Pro Tyr Asp Phe Gly Ser Phe Arg Phe Asp Pro Ile Arg Glu Ser
            35                  40                  45

Ile Val Ser Arg Glu Met Thr Arg Arg Tyr Met Ile Asp Met Val Thr
        50                  55                  60

His Ala Asp Thr Asp Val Val Ile Val Gly Ala Gly Ser Ala Gly Leu
    65                  70                  75                  80

Ser Cys Ala Xaa Glu Leu Ser Lys Asn Pro Ser Asn Asn Xaa Ala Ile
                85                  90                  95

Val Glu Xaa Ser Val Xaa Pro Gly Gly Gly Xaa Trp Val Gly Gly Gln
                100                 105                 110

Leu
```

<210> SEQ ID NO 11
<211> LENGTH: 535
<212> TYPE: DNA
<213> ORGANISM: Triticum aestivum
<220> FEATURE:
<221> NAME/KEY: unsure
<222> LOCATION: (497)

<400> SEQUENCE: 11

```
gccactcgca cccctcctg tgccgccacc cggcgcaccg gggccatctg caactccatc       60
tcctcctgca ccctcccta tgatctcagt tccttcaagt tcagccccat gaaagaatct      120
gtcgcctccc gtgagatgat ccgacggtac atgaccgaca tgatcgccga tgtcaacacc     180
gatgtcatca tcatcggaac tggcagcgcg ggactgtcct gcgcctacga gctctccaag     240
gacccgtctg ttaacatcgc catcatccaa cggtccgttt ccctggcgg cagcggctgg      300 ctcgcagcc agctcttctc cgccatggtc gtgcgcaagc cggcgcacct cttcctcgat      360
gaactcaaca tcgagtacga cgagcaggag gactacgtgg tcatcaagca tgctgcgctc     420
```

```
ttcacctcca ccgtgctgag ccgcctcctc gcgcgggcca acgtgaagct ctttaacggg      480
tctcgtggaa gactggntgt caaagacatc gcgtcacggt gtgtcacaac tgggc           535
```

<210> SEQ ID NO 12
<211> LENGTH: 146
<212> TYPE: PRT
<213> ORGANISM: Triticum aestivum

<400> SEQUENCE: 12

```
Gly Ala Ile Cys Asn Ser Ile Ser Ser Cys Thr Pro Pro Tyr Asp Leu
  1               5                  10                  15

Ser Ser Phe Lys Phe Ser Pro Met Lys Glu Ser Val Ala Ser Arg Glu
             20                  25                  30

Met Ile Arg Arg Tyr Met Thr Asp Met Ile Ala Asp Val Asn Thr Asp
         35                  40                  45

Val Ile Ile Ile Gly Thr Gly Ser Ala Gly Leu Ser Cys Ala Tyr Glu
     50                  55                  60

Leu Ser Lys Asp Pro Ser Val Asn Ile Ala Ile Ile Gln Arg Ser Val
 65                  70                  75                  80

Ser Pro Gly Gly Ser Gly Trp Leu Gly Ser Gln Leu Phe Ser Ala Met
                 85                  90                  95

Val Val Arg Lys Pro Ala His Leu Phe Leu Asp Glu Leu Asn Ile Glu
            100                 105                 110

Tyr Asp Glu Gln Glu Asp Tyr Val Val Ile Lys His Ala Ala Leu Phe
        115                 120                 125

Thr Ser Thr Val Leu Ser Arg Leu Leu Ala Arg Ala Asn Val Lys Leu
    130                 135                 140

Phe Asn
145
```

<210> SEQ ID NO 13
<211> LENGTH: 462
<212> TYPE: DNA
<213> ORGANISM: Zea mays
<220> FEATURE:
<221> NAME/KEY: unsure
<222> LOCATION: (448)
<221> NAME/KEY: unsure
<222> LOCATION: (458)

<400> SEQUENCE: 13

```
ggtcctcaag gttccattcc ggagagtcca tttgactgga gatcagaagc actttgatac      60
atatgacacc agtggtcctc aaaatataag cccaaggatt ggactcccaa agataaggaa     120
ggaatggatt gataggaggg aaaagctggg tagtcctcgg tacacacaaa tgtattatgc     180
taaacaggga attgtaacag aggagatgtt atactgtgcc agccgtgaga accttagtcc     240
tgaatttgtt cggacagaag ttgcccgtgg acgagccata attccttcca acaagaggca     300
cctggaattg gaacccatga ttgttggaag aaacttcctt gtaaaggtga atgcaaatat     360
tgggaattca gctgttgtga gctccattga ggaggaagtt cacaagctcc agtgggccac     420
gatgtgggga gctgatactg tcatggnact ttcaacangg cg                        462
```

<210> SEQ ID NO 14
<211> LENGTH: 98
<212> TYPE: PRT
<213> ORGANISM: Zea mays
<220> FEATURE:
<221> NAME/KEY: UNSURE

<222> LOCATION: (95)

<400> SEQUENCE: 14

Thr Gln Met Tyr Tyr Ala Lys Gln Gly Ile Val Thr Glu Glu Met Leu
1               5                  10                  15

Tyr Cys Ala Ser Arg Glu Asn Leu Ser Pro Glu Phe Val Arg Thr Glu
                20                  25                  30

Val Ala Arg Gly Arg Ala Ile Ile Pro Ser Asn Lys Arg His Leu Glu
            35                  40                  45

Leu Glu Pro Met Ile Val Gly Arg Asn Phe Leu Val Lys Val Asn Ala
        50                  55                  60

Asn Ile Gly Asn Ser Ala Val Val Ser Ser Ile Glu Glu Glu Val His
65                  70                  75                  80

Lys Leu Gln Trp Ala Thr Met Trp Gly Ala Asp Thr Val Met Xaa Leu
                85                  90                  95

Ser Thr

<210> SEQ ID NO 15
<211> LENGTH: 571
<212> TYPE: DNA
<213> ORGANISM: Oryza sativa
<220> FEATURE:
<221> NAME/KEY: unsure
<222> LOCATION: (499)
<221> NAME/KEY: unsure
<222> LOCATION: (548)
<221> NAME/KEY: unsure
<222> LOCATION: (571)

<400> SEQUENCE: 15
gttctaaccg agttcctcac ttcctcctcc gcccgcgtcg cccctcctct cctctccctc      60
ccggctcccg gctaccgccg ccgccgcccc gaggaaatgg ctgccctgca accctcattc     120
tcttcagtcc ctattgggac ggtgcctatt taccaagcac ttgagaaagt taatggtatt     180
gctgaaaatc taagctggga agtctttaga gatactttaa tcgaacaagc tgagcagggt     240
gttgattact tcacaatcca tgctggcgtg cttcttcgtt acattcctct tacggcaaag     300
agaatgaccg gcatagtttc acgtggtggc tctatccatg caaaatggtg cctaacatat     360
cataaggaga actttgccta tgagcactgg gatgaaattc ttgatatttg caatcagtat     420
gatgtggcat tatccattgg cgatggtttg agaccaggtt ctatttatga tgcaaatgat     480
agtgctcagt ttgcagaant gctgactcaa ggggaactca cacgccgaac ttgggcaaaa     540
gattgcangt aatgaatgaa ggccaaggca n                                    571

<210> SEQ ID NO 16
<211> LENGTH: 141
<212> TYPE: PRT
<213> ORGANISM: Oryza sativa
<220> FEATURE:
<221> NAME/KEY: UNSURE
<222> LOCATION: (127)

<400> SEQUENCE: 16

Ser Ser Val Pro Ile Gly Thr Val Pro Ile Tyr Gln Ala Leu Glu Lys
1               5                  10                  15

Val Asn Gly Ile Ala Glu Asn Leu Ser Trp Glu Val Phe Arg Asp Thr
                20                  25                  30

Leu Ile Glu Gln Ala Glu Gln Gly Val Asp Tyr Phe Thr Ile His Ala
            35                  40                  45

```
Gly Val Leu Leu Arg Tyr Ile Pro Leu Thr Ala Lys Arg Met Thr Gly
     50                  55                  60

Ile Val Ser Arg Gly Gly Ser Ile His Ala Lys Trp Cys Leu Thr Tyr
 65                  70                  75                  80

His Lys Glu Asn Phe Ala Tyr Glu His Trp Asp Glu Ile Leu Asp Ile
                 85                  90                  95

Cys Asn Gln Tyr Asp Val Ala Leu Ser Ile Gly Asp Gly Leu Arg Pro
                100                 105                 110

Gly Ser Ile Tyr Asp Ala Asn Asp Ser Ala Gln Phe Ala Glu Xaa Leu
            115                 120                 125

Thr Gln Gly Glu Leu Thr Arg Arg Thr Trp Ala Lys Asp
    130                 135                 140
```

```
<210> SEQ ID NO 17
<211> LENGTH: 442
<212> TYPE: DNA
<213> ORGANISM: Glycine max
<220> FEATURE:
<221> NAME/KEY: unsure
<222> LOCATION: (160)
<221> NAME/KEY: unsure
<222> LOCATION: (426)
<221> NAME/KEY: unsure
<222> LOCATION: (430)
<221> NAME/KEY: unsure
<222> LOCATION: (442)

<400> SEQUENCE: 17
gggacaccct gattgaacaa gctgagcagg gtgtggatta cttcaccatc catgcaggag     60
ttcttctgag atacgttcca ttaacggcta agcgcatgac aggaatagtc tcaagaggag    120
ggtctattca tgcaaagtgg tgcttagctt atcacaaagn gaattttgct tatgagcact    180
gggatgagat acttgacatc tgcaatcagt atgatgtggc cctatccatt ggtgatgggc    240
taagacctgg atccatctat gatgcaaatg acacagctca gttcgccgaa ctcttgacac    300
aaggagaatt gacccgtaga gcatgggaga aggatgtaca ggtgatgaat gaaggacctg    360
gacatgtccc aatgcacaag attcctgaaa catgcagaac agttagatgg tgtagtaagc    420
cctttnacan cttgggcctt tn                                             442
```

```
<210> SEQ ID NO 18
<211> LENGTH: 127
<212> TYPE: PRT
<213> ORGANISM: Glycine max
<220> FEATURE:
<221> NAME/KEY: UNSURE
<222> LOCATION: (53)

<400> SEQUENCE: 18

Asp Thr Leu Ile Glu Gln Ala Glu Gln Gly Val Asp Tyr Phe Thr Ile
  1               5                  10                  15

His Ala Gly Val Leu Leu Arg Tyr Val Pro Leu Thr Ala Lys Arg Met
             20                  25                  30

Thr Gly Ile Val Ser Arg Gly Gly Ser Ile His Ala Lys Trp Cys Leu
         35                  40                  45

Ala Tyr His Lys Xaa Asn Phe Ala Tyr Glu His Trp Asp Glu Ile Leu
     50                  55                  60

Asp Ile Cys Asn Gln Tyr Asp Val Ala Leu Ser Ile Gly Asp Gly Leu
 65                  70                  75                  80

Arg Pro Gly Ser Ile Tyr Asp Ala Asn Asp Thr Ala Gln Phe Ala Glu
                 85                  90                  95
```

```
Leu Leu Thr Gln Gly Glu Leu Thr Arg Arg Ala Trp Glu Lys Asp Val
            100                 105                 110

Gln Val Met Asn Glu Gly Pro Gly His Val Pro Met His Lys Ile
        115                 120                 125

<210> SEQ ID NO 19
<211> LENGTH: 534
<212> TYPE: DNA
<213> ORGANISM: Triticum aestivum
<220> FEATURE:
<221> NAME/KEY: unsure
<222> LOCATION: (445)
<221> NAME/KEY: unsure
<222> LOCATION: (520)
<221> NAME/KEY: unsure
<222> LOCATION: (523)
<221> NAME/KEY: unsure
<222> LOCATION: (532)

<400> SEQUENCE: 19
acgaaacaca cagttgatcc tgctgctccc gaatttctgc cgctcccagc atttgaagac      60
tgcttcccac ggagcaccaa agaatgcagt gaagtcgttc atgaggaaac aggtcatgcc     120
ctgaaggttc catttcggag agtccatttg accggagata gcgggcattt cgacacatat     180
gacaccagtg gtccacaaaa cataagccca aggctcggac tcccaaagat aagaaaggaa     240
tggattgaca ggagagagaa gttgggtagt cctcgttaca cgcaaatgta ctatgctaag     300
cagggaatca taacagagga gatactgtac tgtgccaaac gcgagaacct tgctcctgaa     360
tttgtccggt cagaagtcgc ccgtggacga gccattatcc cttccaacaa agaggcacct     420
ggaattggaa cccatgattg ttggnagaaa cttccttgta aggtgaatg ctaacattgg      480 ggaaccccgg ctgttgtgag ctccaattga gggggaagn canaagctcc antg            534

<210> SEQ ID NO 20
<211> LENGTH: 136
<212> TYPE: PRT
<213> ORGANISM: Triticum aestivum

<400> SEQUENCE: 20

Ser Thr Lys Glu Cys Ser Glu Val Val His Glu Thr Gly His Ala
 1               5                   10                  15

Leu Lys Val Pro Phe Arg Arg Val His Leu Thr Gly Asp Ser Gly His
                 20                  25                  30

Phe Asp Thr Tyr Asp Thr Ser Gly Pro Gln Asn Ile Ser Pro Arg Leu
             35                  40                  45

Gly Leu Pro Lys Ile Arg Lys Glu Trp Ile Asp Arg Arg Glu Lys Leu
     50                  55                  60

Gly Ser Pro Arg Tyr Thr Gln Met Tyr Tyr Ala Lys Gln Gly Ile Ile
 65                  70                  75                  80

Thr Glu Glu Ile Leu Tyr Cys Ala Lys Arg Glu Asn Leu Ala Pro Glu
                 85                  90                  95

Phe Val Arg Ser Glu Val Ala Arg Gly Arg Ala Ile Ile Pro Ser Asn
            100                 105                 110

Lys Glu His Leu Glu Leu Glu Pro Met Ile Val Gly Arg Asn Phe Leu
        115                 120                 125

Val Lys Val Asn Ala Asn Ile Gly
    130                 135

<210> SEQ ID NO 21
```

<211> LENGTH: 1405
<212> TYPE: DNA
<213> ORGANISM: Oryza sativa

<400> SEQUENCE: 21

```
gcacgaggtt taaaccagag caagaagctc agctcctcct cctctcgcat ggcagccatg      60
gccaccaccg cgtccagcct cctcaagacc tccttcgctg gcgcgcgcct ccccgccgcc     120
gcccgcaacc ccaccgtctc cgtcgcgccg cgcaccggcg gcgccatctg caactccatc     180
tcgtcgtcgt cgtccactcc cccctacgac ctcaacgcca tcaggttcag ccccatcaag     240
gagtccatcg tgtctcgcga gatgacccgg cggtacatga ccgacatgat cacctacgcc     300
gacaccgacg tcgtcgtcgt cggcgccggc tccgcgggc tctcctgcgc gtacgagctc      360
tccaaggacc cctccgtcag cgtcgccgtc atcgagcagt cggtgtcccc cggcggcggc     420
gcgtggctcg gcgggcagct gttctccgcc atggtggtgc gcaagccggc gcacctgttc     480
ctcgacgagc tcggcgtcgc gtacgacgag caggaggact acgtcgtcat caagcacgcc     540
gcgctcttca cctccaccgt catgagccgc ctcctggcgc gccccaacgt gaagctgttc     600
aacgccgtcg ccgtcgagga cctcatcgtc aaggagggcc gcgtcggcgg cgtggtcacc     660
aactgggcgc tggtgtcgat gaaccacgac acgcagtcgt gcatggaccc caacgtgatg     720
gagtccaggg tggtggtgag ctcctgcggc cacgacgggc cgttcggcgc cacgggcgtc     780
aagcggctgc aggacatcgg catgatcgac gccgtgcccg gcatgcgcgc cctcgacatg     840
aacaccgccg aggacgagat cgtccgcctc acccgcgagg tcgtccccgg catgatcgtc     900
accggcatgg aggtcgccga gatcgacggc gccccgagaa tgggcccgac gttcggagcc     960
atgatgatct ccggccagaa ggcggcgcac ctggcgctga aggcgctcgg ccggccgaac    1020
gccatcgacg gcacgatcaa gaaggcggcg gcggcggcgg cgcacccgga gctgatcctg    1080
gcgtcgaagg acgacggcga gatcgtggac gcctgagcga atagaacagg gtaaaaaaaa    1140
atccgcaaga cgtggtggtg acacggagga gttgggacg agaagaagat gtggactttc     1200
ccctgtgttt ttttttcggg atttgcattg atccccttgt ttgttttagc tctggatgtt    1260
gattagcgtc ttgttcatag cacttccact gccaccgtgt gtgtgtgctc tgcttgcctg    1320
atgagggcaa gaaacttcc atggatccgt ctctctggga ggaatgaata aaaggatga     1380
ggaaataaaa aaaaaaaaaa aaaaa                                         1405
```

<210> SEQ ID NO 22
<211> LENGTH: 355
<212> TYPE: PRT
<213> ORGANISM: Oryza sativa

<400> SEQUENCE: 22

```
Met Ala Ala Met Ala Thr Thr Ala Ser Ser Leu Leu Lys Thr Ser Phe
 1               5                  10                  15

Ala Gly Ala Arg Leu Pro Ala Ala Arg Asn Pro Thr Val Ser Val
            20                  25                  30

Ala Pro Arg Thr Gly Gly Ala Ile Cys Asn Ser Ile Ser Ser Ser
        35                  40                  45

Ser Thr Pro Pro Tyr Asp Leu Asn Ala Ile Arg Phe Ser Pro Ile Lys
    50                  55                  60

Glu Ser Ile Val Ser Arg Glu Met Thr Arg Arg Tyr Met Thr Asp Met
65                  70                  75                  80

Ile Thr Tyr Ala Asp Thr Asp Val Val Val Gly Ala Gly Ser Ala
                85                  90                  95
```

-continued

```
Gly Leu Ser Cys Ala Tyr Glu Leu Ser Lys Asp Pro Ser Val Ser Val
                100                 105                 110

Ala Val Ile Glu Gln Ser Val Ser Pro Gly Gly Ala Trp Leu Gly
        115                 120                 125

Gly Gln Leu Phe Ser Ala Met Val Val Arg Lys Pro Ala His Leu Phe
    130                 135                 140

Leu Asp Glu Leu Gly Val Ala Tyr Asp Glu Gln Asp Tyr Val Val
145                 150                 155                 160

Ile Lys His Ala Ala Leu Phe Thr Ser Thr Val Met Ser Arg Leu Leu
                165                 170                 175

Ala Arg Pro Asn Val Lys Leu Phe Asn Ala Val Ala Val Glu Asp Leu
            180                 185                 190

Ile Val Lys Glu Gly Arg Val Gly Val Val Thr Asn Trp Ala Leu
        195                 200                 205

Val Ser Met Asn His Asp Thr Gln Ser Cys Met Asp Pro Asn Val Met
    210                 215                 220

Glu Ser Arg Val Val Ser Ser Cys Gly His Asp Gly Pro Phe Gly
225                 230                 235                 240

Ala Thr Gly Val Lys Arg Leu Gln Asp Ile Gly Met Ile Asp Ala Val
                245                 250                 255

Pro Gly Met Arg Ala Leu Asp Met Asn Thr Ala Glu Asp Glu Ile Val
            260                 265                 270

Arg Leu Thr Arg Glu Val Val Pro Gly Met Ile Val Thr Gly Met Glu
        275                 280                 285

Val Ala Glu Ile Asp Gly Ala Pro Arg Met Gly Pro Thr Phe Gly Ala
    290                 295                 300

Met Met Ile Ser Gly Gln Lys Ala Ala His Leu Ala Leu Lys Ala Leu
305                 310                 315                 320

Gly Arg Pro Asn Ala Ile Asp Gly Thr Ile Lys Lys Ala Ala Ala
                325                 330                 335

Ala Ala His Pro Glu Leu Ile Leu Ala Ser Lys Asp Asp Gly Glu Ile
            340                 345                 350

Val Asp Ala
    355
```

<210> SEQ ID NO 23
<211> LENGTH: 1211
<212> TYPE: DNA
<213> ORGANISM: Glycine max

<400> SEQUENCE: 23

```
gcaccagcca aatatcatca tctgaaacga tggctgccat ggcaaccaca accctctctt    60
caaacccgaa actctcattt ttccacggaa agcccgttac atattcttcc cgcgtcgcac   120
ccaccaccaa gttattctca tccaaacaag gcacaatctc catgtcccta acccaacccc   180
catacgacct ccaatccttc aaattccaac ccatcaaaga atccatcgtc tcacgcgaaa   240
tgacgcgccg ctacatgacc gacatgataa cctacgccga caccgacgtc gtaatcgtcg   300
gagccggctc ggcggggctc tcctgtgcgt acgagatcag caagaacccc gccgtgagcg   360
tcgccataat cgagcagtcc gtgagcccg gcggcggcgc gtggctcggc ggacaactct   420
tctccgccat ggtggttcgc aagccggcgc acctcttcct ggacgagctc ggcgtggcgt   480
acgacgagca agaggactac gttgtgataa agcacgcggc tttgttcacg tccaccatca   540
tgagcaggct tctagcgagg cccaacgtga agctcttcaa cgcggtggcg gcggaggact   600
```

-continued

```
tgatcgtgaa ggaagggagg gttgcagggg ttgtgaccaa ctgggctctg gtttcgatga      660
accatgacac gcagtcttgc atggacccca acgtgatgga ggctaaggtt gttgtgagct      720
cttgtgggca cgatggacct tttggcgcca ccggggttaa gaggttgaag agtattggca      780
tgattgatag cgttcctgga atgaaggctt ggatatgaa tgctgcagag gatgctattg       840
tgaggctcac gagggagatt gtgcccggca tgattgtcac cggcatggag gtggcagaaa      900
ttgatggctc cccaaggatg ggtccgacgt ttggggcgat gatgatatca gggcagaagg      960
cggctcattt ggcgttgaag gcgttgggga ggaacaatgc aattgatgga acgtgtggag     1020
ttggaaggga agaaccccag cttattttcg cttctgcaga cactgaggaa attgttgatg     1080
cttaaactta ctttcaaatt agctagatat atagctttc ttttcttttc tttctgtttg      1140
gtccctactt aattatgatt ttaattttgg aataaatgaa caacatgtga attaaaaaaa     1200 aaaaaaaaa a                                                           1211
```

<210> SEQ ID NO 24
<211> LENGTH: 351
<212> TYPE: PRT
<213> ORGANISM: Glycine max

<400> SEQUENCE: 24

```
Met Ala Ala Met Ala Thr Thr Thr Leu Ser Ser Asn Pro Lys Leu Ser
  1               5                  10                  15

Phe Phe His Gly Lys Pro Val Thr Tyr Ser Ser Arg Val Ala Pro Thr
                 20                  25                  30

Thr Lys Leu Phe Ser Ser Lys Gln Gly Thr Ile Ser Met Ser Leu Thr
             35                  40                  45

Gln Pro Pro Tyr Asp Leu Gln Ser Phe Lys Phe Gln Pro Ile Lys Glu
         50                  55                  60

Ser Ile Val Ser Arg Glu Met Thr Arg Tyr Met Thr Asp Met Ile
 65                  70                  75                  80

Thr Tyr Ala Asp Thr Asp Val Val Ile Val Gly Ala Gly Ser Ala Gly
                 85                  90                  95

Leu Ser Cys Ala Tyr Glu Ile Ser Lys Asn Pro Ala Val Ser Val Ala
                100                 105                 110

Ile Ile Glu Gln Ser Val Ser Pro Gly Gly Gly Ala Trp Leu Gly Gly
            115                 120                 125

Gln Leu Phe Ser Ala Met Val Arg Lys Pro Ala His Leu Phe Leu
        130                 135                 140

Asp Glu Leu Gly Val Ala Tyr Asp Glu Gln Glu Asp Tyr Val Val Ile
145                 150                 155                 160

Lys His Ala Ala Leu Phe Thr Ser Thr Ile Met Ser Arg Leu Leu Ala
                165                 170                 175

Arg Pro Asn Val Lys Leu Phe Asn Ala Val Ala Glu Asp Leu Ile
                180                 185                 190

Val Lys Glu Gly Arg Val Ala Gly Val Val Thr Asn Trp Ala Leu Val
            195                 200                 205

Ser Met Asn His Asp Thr Gln Ser Cys Met Asp Pro Asn Val Met Glu
        210                 215                 220

Ala Lys Val Val Ser Ser Cys Gly His Asp Gly Pro Phe Gly Ala
225                 230                 235                 240

Thr Gly Val Lys Arg Leu Lys Ser Ile Gly Met Ile Asp Ser Val Pro
                245                 250                 255
```

```
Gly Met Lys Ala Leu Asp Met Asn Ala Glu Asp Ala Ile Val Arg
            260                 265                 270

Leu Thr Arg Glu Ile Val Pro Gly Met Ile Val Thr Gly Met Glu Val
        275                 280                 285

Ala Glu Ile Asp Gly Ser Pro Arg Met Gly Pro Thr Phe Gly Ala Met
    290                 295                 300

Met Ile Ser Gly Gln Lys Ala Ala His Leu Ala Leu Lys Ala Leu Gly
305                 310                 315                 320

Arg Asn Asn Ala Ile Asp Gly Thr Cys Gly Val Gly Arg Glu Glu Pro
                325                 330                 335

Gln Leu Ile Phe Ala Ser Ala Asp Thr Glu Glu Ile Val Asp Ala
            340                 345                 350

<210> SEQ ID NO 25
<211> LENGTH: 1381
<212> TYPE: DNA
<213> ORGANISM: Triticum aestivum

<400> SEQUENCE: 25
gcacgagcac agctccacac accatggcag ccatggccac caccgcctcc agcctcctca      60
agccctcctt ctccggcgtc cgcctcccgg cggcggcccg caccccgtcc tgcgtcgcca     120
ccccgcgtgc cggcgccatc tgcaactcca tctcctcctc cacacctccc tacgacctca     180
acgccttcaa gttcagcccc atcaaggagt ccatcgtgtc ccgcgagatg acccgccgct     240
acatgaccga catgatcacc tacgccgaca ccgacgtcgt catcgtcggc gccggatccg     300
cggggctttc ctgcgcgtac gagctctcca aggacccctc catcagcatc gccatcatcg     360
agcagtccgt gtccccggc ggcggcgcct ggctcggcgg ccagctcttc tccgccatgg     420
tcgtgcgcaa gccggcgcac ctcttcctcg acgagctcaa catcgagtac gacgagcagg     480
aggactacgt cgtcatcaag cacgccgcgc tcttcacctc cacggtcatg agccgcctcc     540
tcgcgcgccc caacgtcaag ctcttcaacg ccgtcgccgt ggaggacctc atcgtcaagg     600
aggaccgcgt cgccggcgtc gtcaccaact gggcgctcgt ctccatgaac acgacacac      660
agtcctgcat ggaccccaac gtcatggagg ccaaggtcgt ggtgagctct gcggccacg      720
acgggcccctt cggcgccacc ggggtcaagc ggctccagga catcggcatg atccaggcgg     780
tgcccgggat gaaggcgctc gacatgaaca cggccgagga tgccatcgtg cgcctcaccc     840
gggaggtggt cccccggcatg attgtcaccg gcatggaggt cgccgagatc gacggcgccc     900
cgagaatggg cccgaccttc ggcgccatga tgatctccgg ccagaaggcg gcgcacctgg     960
cgctcaaggc cctcggccgg ccgaacggca tcgacgggac gctcaagaac gtgaccccgg    1020
cgctgcaccc ggagatgatc ctggcggcga ccaacaacgg cgacatcgtg gacgcctaag    1080
caaagcaatg aaccacggac accaaggcgt acgtacgctg gtgtttcggg gcgaaaaatc    1140
aataagatgg ttcggtgaaa cagaggatgc ttagggacga ggtcttgtct ttgtgatttg    1200
tcagactcgt gtttaattcc gatgtttatc tttagttttc ttgtgttagc gtattttgtt    1260
catgccacct gcccgccatg tgctctgctc tgctctgcct cacggcagct ccatggatga    1320
tgaatcctta tggaacaaga ggagggaata aaaggttga gttctaaaaa aaaaaaaaa     1380
a                                                                   1381

<210> SEQ ID NO 26
<211> LENGTH: 351
<212> TYPE: PRT
<213> ORGANISM: Triticum aestivum
```

<400> SEQUENCE: 26

```
Met Ala Ala Met Ala Thr Thr Ala Ser Ser Leu Leu Lys Pro Ser Phe
  1               5                  10                  15
Ser Gly Val Arg Leu Pro Ala Ala Arg Thr Pro Ser Cys Val Ala
             20                  25                  30
Thr Pro Arg Ala Gly Ala Ile Cys Asn Ser Ile Ser Ser Thr Pro
             35                  40                  45
Pro Tyr Asp Leu Asn Ala Phe Lys Phe Ser Pro Ile Lys Glu Ser Ile
 50                  55                  60
Val Ser Arg Glu Met Thr Arg Arg Tyr Met Thr Asp Met Ile Thr Tyr
 65                  70                  75                  80
Ala Asp Thr Asp Val Val Ile Val Gly Ala Gly Ser Ala Gly Leu Ser
             85                  90                  95
Cys Ala Tyr Glu Leu Ser Lys Asp Pro Ser Ile Ser Ile Ala Ile Ile
            100                 105                 110
Glu Gln Ser Val Ser Pro Gly Gly Gly Ala Trp Leu Gly Gly Gln Leu
            115                 120                 125
Phe Ser Ala Met Val Val Arg Lys Pro Ala His Leu Phe Leu Asp Glu
130                 135                 140
Leu Asn Ile Glu Tyr Asp Glu Gln Glu Asp Tyr Val Val Ile Lys His
145                 150                 155                 160
Ala Ala Leu Phe Thr Ser Thr Val Met Ser Arg Leu Leu Ala Arg Pro
                165                 170                 175
Asn Val Lys Leu Phe Asn Ala Val Ala Val Glu Asp Leu Ile Val Lys
                180                 185                 190
Glu Asp Arg Val Ala Gly Val Val Thr Asn Trp Ala Leu Val Ser Met
                195                 200                 205
Asn His Asp Thr Gln Ser Cys Met Asp Pro Asn Val Met Glu Ala Lys
210                 215                 220
Val Val Val Ser Ser Cys Gly His Asp Gly Pro Phe Gly Ala Thr Gly
225                 230                 235                 240
Val Lys Arg Leu Gln Asp Ile Gly Met Ile Gln Ala Val Pro Gly Met
                245                 250                 255
Lys Ala Leu Asp Met Asn Thr Ala Glu Asp Ala Ile Val Arg Leu Thr
                260                 265                 270
Arg Glu Val Val Pro Gly Met Ile Val Thr Gly Met Glu Val Ala Glu
                275                 280                 285
Ile Asp Gly Ala Pro Arg Met Gly Pro Thr Phe Gly Ala Met Met Ile
290                 295                 300
Ser Gly Gln Lys Ala Ala His Leu Ala Leu Lys Ala Leu Gly Arg Pro
305                 310                 315                 320
Asn Gly Ile Asp Gly Thr Leu Lys Asn Val Thr Pro Ala Leu His Pro
                325                 330                 335
Glu Met Ile Leu Ala Ala Thr Asn Asn Gly Asp Ile Val Asp Ala
                340                 345                 350
```

<210> SEQ ID NO 27
<211> LENGTH: 636
<212> TYPE: DNA
<213> ORGANISM: Oryza sativa

<400> SEQUENCE: 27
gcacgagtac acatggagtc cagggtggtg gtgagctcct gcggccacga cgggccgttc    60

-continued

```
ggcgccacgg gcgtcaagcg gctgcaggac atcggcatga tcgacgccgt gcccggcatg      120
cgcgccctcg acatgaacac cgccgaggac gagatcgtcc gcctcacccg cgaggtcgtc      180
cccggcatga tcgtcaccgg catggaggtc gccgagatcg acggcgcccc gagaatgggc      240
ccgacgttcg gagccatgat gatctccggc cagaaggcgg cgcacctggc gctgaaggcg      300
ctcggccggc cgaacgccat cgacggcacg atcaagaagg cggcggcggc ggcggcgcac      360
ccggagctga tcctggcgtc gaaggacgac ggcgagatcg tggacgcctg agcgaataga      420
acagggtaaa aaaaatccg caagacgtgg tggtgacacg gaggagttgg ggacgagaag       480
aagatgtgga ctttccctg tgttttttt tcgggatttg cattgatccc cttgtttgtt       540
ttagctctgg atgttgatta gcgtcttgtt catagcactt ccactgccaa aaaaaaaaa      600 aaaaaaaaa aaaaaaaaa aaaaaaaaa aaaaaa                                 636
```

<210> SEQ ID NO 28
<211> LENGTH: 136
<212> TYPE: PRT
<213> ORGANISM: Oryza sativa

<400> SEQUENCE: 28

```
Ala Arg Val His Met Glu Ser Arg Val Val Ser Ser Cys Gly His
 1               5                  10                  15

Asp Gly Pro Phe Gly Ala Thr Gly Val Lys Arg Leu Gln Asp Ile Gly
                20                  25                  30

Met Ile Asp Ala Val Pro Gly Met Arg Ala Leu Asp Met Asn Thr Ala
            35                  40                  45

Glu Asp Glu Ile Val Arg Leu Thr Arg Glu Val Val Pro Gly Met Ile
        50                  55                  60

Val Thr Gly Met Glu Val Ala Glu Ile Asp Gly Ala Pro Arg Met Gly
    65                  70                  75                  80

Pro Thr Phe Gly Ala Met Met Ile Ser Gly Gln Lys Ala Ala His Leu
                85                  90                  95

Ala Leu Lys Ala Leu Gly Arg Pro Asn Ala Ile Asp Gly Thr Ile Lys
            100                 105                 110

Lys Ala Ala Ala Ala Ala His Pro Glu Leu Ile Leu Ala Ser Lys
        115                 120                 125

Asp Asp Gly Glu Ile Val Asp Ala
    130                 135
```

<210> SEQ ID NO 29
<211> LENGTH: 1215
<212> TYPE: DNA
<213> ORGANISM: Triticum aestivum

<400> SEQUENCE: 29

```
gcacgaggcc actcgcaccc cctcctgtgc cgccacccgg cgcaccgggg ccatctgcaa       60
ctccatctcc tcctgcaccc ctccctatga tctcagttcc ttcaagttca gccccatgaa      120
agaatctgtc gcctcccgtg agatgatccg acggtacatg accgacatga tcgccgatgt      180
caacaccgat gtcatcatca tcggaactgg cagcgcggga ctgtcctgcg cctacgagct      240
ctccaaggac ccgtctgtta acatcgccat catccaacgg tccgtttccc ctggcggcag      300
cggctggctc ggcagccagc tcttctccgc catggtcgtg gcaagccgg cgcacctctt       360 cctcgatgaa ctcaacatcg agtacgacga gcaggaggac tacgtggtca tcaagcatgc      420
tgcgctcttc acctccaccg tgctgagccg cctcctcgcg cggcccaacg tgaagctctt      480
```

-continued

```
taacggcgtc gtcgtggaag acttggttgt caaagagcat cgcgtcaccg gtgtggtcac    540
caactgggcg ctcgtgtcga tgaaccagga cacacactca caaacacaat cacacatgga    600
cgccaacgtc atggaagcca agatcgtagt aagctcatgt ggccacgagg ggctattcag    660
tgccaacgga aagggagtca acggctcgag gacatcgga atgatcaaga cggtgccccg     720
aaccggaatg gaagcgcttg acacgaacgt atccgaggat gcaattgttg cttaacccg     780 cgaggtcgtc cccggcatga tcgtcgctgg cattgaggtt gccgagatcg acgggcccca    840
gaggatgtgc ccaacgttcg cgccacgat tatctccggc cagaaggcag cgcacctggc     900
actcaaggcg ctcggccgtc cgaacggcat cgactcggag acggtcccag cgtgaggacc    960
agcggcgaca ccatggacgc ctggacgacg gaggtgacac caaagcgtcc gctggtgttt   1020
gatggaacag aggagacttt ggacgaagac tttatatatg tcatctgtct acttgtgttt   1080 aatcccttg ttcatctcta atactactag tagcagcgtc ttgttcatag cactgccgcc    1140
gtgtgccctt ccccgtgacg gcaactccat ggatcctcct ggaacaagat gacagaataa   1200
aatggttggg cttcc                                                   1215
```

<210> SEQ ID NO 30
<211> LENGTH: 317
<212> TYPE: PRT
<213> ORGANISM: Triticum aestivum

<400> SEQUENCE: 30

```
His Glu Ala Thr Arg Thr Pro Ser Cys Ala Ala Thr Arg Arg Thr Gly
  1               5                  10                  15

Ala Ile Cys Asn Ser Ile Ser Ser Cys Thr Pro Pro Tyr Asp Leu Ser
             20                  25                  30

Ser Phe Lys Phe Ser Pro Met Lys Glu Ser Val Ala Ser Arg Glu Met
         35                  40                  45

Ile Arg Arg Tyr Met Thr Asp Met Ile Ala Asp Val Asn Thr Asp Val
     50                  55                  60

Ile Ile Ile Gly Thr Gly Ser Ala Gly Leu Ser Cys Ala Tyr Glu Leu
 65                  70                  75                  80

Ser Lys Asp Pro Ser Val Asn Ile Ala Ile Ile Gln Arg Ser Val Ser
                 85                  90                  95

Pro Gly Gly Ser Gly Trp Leu Gly Ser Gln Leu Phe Ser Ala Met Val
            100                 105                 110

Val Arg Lys Pro Ala His Leu Phe Leu Asp Glu Leu Asn Ile Glu Tyr
        115                 120                 125

Asp Glu Gln Glu Asp Tyr Val Val Ile Lys His Ala Ala Leu Phe Thr
    130                 135                 140

Ser Thr Val Leu Ser Arg Leu Leu Ala Arg Pro Asn Val Lys Leu Phe
145                 150                 155                 160

Asn Gly Val Val Glu Asp Leu Val Val Lys Glu His Arg Val Thr
                165                 170                 175

Gly Val Val Thr Asn Trp Ala Leu Val Ser Met Asn Gln Asp Thr His
            180                 185                 190

Ser Gln Thr Gln Ser His Met Asp Ala Asn Val Met Glu Ala Lys Ile
        195                 200                 205

Val Val Ser Ser Cys Gly His Glu Gly Leu Phe Ser Ala Asn Gly Lys
    210                 215                 220

Gly Val Lys Arg Leu Glu Asp Ile Gly Met Ile Lys Thr Val Pro Arg
225                 230                 235                 240
```

```
Thr Gly Met Glu Ala Leu Asp Thr Asn Val Ser Glu Asp Ala Ile Val
            245                 250                 255
Gly Leu Thr Arg Glu Val Val Pro Gly Met Ile Val Ala Gly Ile Glu
        260                 265                 270
Val Ala Glu Ile Asp Gly Pro Gln Arg Met Cys Pro Thr Phe Gly Ala
        275                 280                 285
Thr Ile Ile Ser Gly Gln Lys Ala Ala His Leu Ala Leu Lys Ala Leu
        290                 295                 300
Gly Arg Pro Asn Gly Ile Asp Ser Glu Thr Val Pro Ala
305                 310                 315
```

<210> SEQ ID NO 31
<211> LENGTH: 1886
<212> TYPE: DNA
<213> ORGANISM: Zea mays

<400> SEQUENCE: 31

```
ccacgcgtcc ggtcctcaag gttccattcc ggagagtcca tttgactgga gatcagaagc      60
actttgatac atatgacacc agtggtcctc aaaatataag cccaaggatt ggactcccaa     120
agataaggaa ggaatggatt gataggaggg aaaagctggg tagtcctcgg tacacacaaa     180
tgtattatgc taaacaggga attgtaacag gagagatgtt atactgtgcc agccgtgaga     240
accttagtcc tgaatttgtt cggacagaag ttgcccgtgg acgagccata attccttcca     300
acaagaggca cctggaattg aacccatga ttgttggaag aaacttcctt gtaaaggtga      360
atgcaaatat tgggaattca gctgttgtga gctccattga ggaggaagtt cacaagctcc     420
agtgggccac gatgtgggga gctgatactg tcatggacct ttcaacaggg cgacatatcc     480
atgagacgcg ggaatggatt attcgcaact ctccggttcc tattgggact gttcctatt      540
accaagcact tgagaaagta atggtattg ctgaaaatct gagctgggaa attttaggg       600
ataccttgat tgaacaagct gagcagggcg ttgattactt cacaatccat gctggtgtcc     660
tgcttcgtta cattcctctt acagcaaaga gaatgacggg catagtttca cgtggtggct     720
caatccatgc aaaatggtgc ttaacttatc acaaggagaa cttttgcatat gaacatttggg    780
atgacattct tgacatatgc aatcagtatg atgtggcatt atcaattggt gatggttttga    840
ggcctggttc catttatgat gcaaatgata gtgcacagtt tgcagaactg ctgactcaag     900
gtgaactaac acgtcgagca tgggcgaaaa atgtgcaggt gatgaatgaa ggcccgggtc     960
acatcccaat gcataaaatt cctgaaaaca tggagaaaca gttggagtgg tgtaatgaag    1020
cgcctttcta tacattgggt cctttgacaa ctgatattgc acctggttat gatcacatca    1080
cttcagccat tggtgctgcc aacattggag ctcttggcac tgcacttctt tgctatgtaa    1140
caccaaagga gcaccttggg ttgcccaatc gtgatgatgt caagactggt gtaatatcct    1200
acaaaatttc tgctcatgct gctgatttgg cgaagggtca tccctatgca caagcttggg    1260
atgatgcact tagcaaggca aggtttgagt ttagatggct tgaccaattt gctttatctc    1320
tggatccagt aactgctatg gctttccatg atgaaacatt gccctctgag ggtgccaaag    1380
tggcacattt ctgctcaatg tgtgggccca gttttgttc aatgaaaatc acggaggata    1440
tcaggaagta tgctgatgaa aatggttatg aacagtaga ggaagctgtg atacaaggaa     1500
tgaatgctat gagtgctgaa ttttggctg caaggaaaac aattagtggg gaacaacatg      1560
gtgaagcagg aggggagatc tatgtaccag aaagctatgc agctcagaaa taaggtttcc    1620
tcggagacat ccattccaaa tgaggctaag gcatcagcag ctgttctggc tagtggctaa    1680
```

```
ggcatcagca gctgttctac catcttatct aatgagatgg taagcagtat gtgaataaag    1740
ctggtgttgc ttaccttcag tttgtgaatg ccattatgta ctgtaataaa aaactctgta    1800
ttgtactccc tagcattatc attatgcttt aaaaaaaaaa aaaaaaaaaa aaaaaaaaaa    1860
aaaaaaaaaa aaaaaaaaaa aaaaag                                        1886
```

<210> SEQ ID NO 32
<211> LENGTH: 536
<212> TYPE: PRT
<213> ORGANISM: Zea mays

<400> SEQUENCE: 32

```
Thr Arg Pro Val Leu Lys Val Pro Phe Arg Arg Val His Leu Thr Gly
  1               5                  10                  15

Asp Gln Lys His Phe Asp Thr Tyr Asp Thr Ser Gly Pro Gln Asn Ile
                 20                  25                  30

Ser Pro Arg Ile Gly Leu Pro Lys Ile Arg Lys Glu Trp Ile Asp Arg
             35                  40                  45

Arg Glu Lys Leu Gly Ser Pro Arg Tyr Thr Gln Met Tyr Tyr Ala Lys
         50                  55                  60

Gln Gly Ile Val Thr Glu Glu Met Leu Tyr Cys Ala Ser Arg Glu Asn
 65                  70                  75                  80

Leu Ser Pro Glu Phe Val Arg Thr Glu Val Ala Arg Gly Arg Ala Ile
                 85                  90                  95

Ile Pro Ser Asn Lys Arg His Leu Glu Leu Glu Pro Met Ile Val Gly
            100                 105                 110

Arg Asn Phe Leu Val Lys Val Asn Ala Asn Ile Gly Asn Ser Ala Val
        115                 120                 125

Val Ser Ser Ile Glu Glu Val His Lys Leu Gln Trp Ala Thr Met
130                 135                 140

Trp Gly Ala Asp Thr Val Met Asp Leu Ser Thr Gly Arg His Ile His
145                 150                 155                 160

Glu Thr Arg Glu Trp Ile Ile Arg Asn Ser Pro Val Pro Ile Gly Thr
                165                 170                 175

Val Pro Ile Tyr Gln Ala Leu Glu Lys Val Asn Gly Ile Ala Glu Asn
            180                 185                 190

Leu Ser Trp Glu Ile Phe Arg Asp Thr Leu Ile Glu Gln Ala Glu Gln
        195                 200                 205

Gly Val Asp Tyr Phe Thr Ile His Ala Gly Val Leu Leu Arg Tyr Ile
    210                 215                 220

Pro Leu Thr Ala Lys Arg Met Thr Gly Ile Val Ser Arg Gly Gly Ser
225                 230                 235                 240

Ile His Ala Lys Trp Cys Leu Thr Tyr His Lys Glu Asn Phe Ala Tyr
                245                 250                 255

Glu His Trp Asp Asp Ile Leu Asp Ile Cys Asn Gln Tyr Asp Val Ala
            260                 265                 270

Leu Ser Ile Gly Asp Gly Leu Arg Pro Gly Ser Ile Tyr Asp Ala Asn
        275                 280                 285

Asp Ser Ala Gln Phe Ala Glu Leu Leu Thr Gln Gly Glu Leu Thr Arg
    290                 295                 300

Arg Ala Trp Ala Lys Asp Val Gln Val Met Asn Glu Gly Pro Gly His
305                 310                 315                 320

Ile Pro Met His Lys Ile Pro Glu Asn Met Glu Lys Gln Leu Glu Trp
                325                 330                 335
```

-continued

```
Cys Asn Glu Ala Pro Phe Tyr Thr Leu Gly Pro Leu Thr Thr Asp Ile
        340                 345                 350

Ala Pro Gly Tyr Asp His Ile Thr Ser Ala Ile Gly Ala Ala Asn Ile
        355                 360                 365

Gly Ala Leu Gly Thr Ala Leu Leu Cys Tyr Val Thr Pro Lys Glu His
        370                 375                 380

Leu Gly Leu Pro Asn Arg Asp Val Lys Thr Gly Val Ile Ser Tyr
385                 390                 395                 400

Lys Ile Ser Ala His Ala Ala Asp Leu Ala Lys Gly His Pro Tyr Ala
                405                 410                 415

Gln Ala Trp Asp Asp Ala Leu Ser Lys Ala Arg Phe Glu Phe Arg Trp
        420                 425                 430

Leu Asp Gln Phe Ala Leu Ser Leu Asp Pro Val Thr Ala Met Ala Phe
        435                 440                 445

His Asp Glu Thr Leu Pro Ser Glu Gly Ala Lys Val Ala His Phe Cys
        450                 455                 460

Ser Met Cys Gly Pro Lys Phe Cys Ser Met Lys Ile Thr Glu Asp Ile
465                 470                 475                 480

Arg Lys Tyr Ala Asp Glu Asn Gly Tyr Gly Thr Val Glu Glu Ala Val
                485                 490                 495

Ile Gln Gly Met Asn Ala Met Ser Ala Glu Phe Leu Ala Ala Arg Lys
        500                 505                 510

Thr Ile Ser Gly Glu Gln His Gly Glu Ala Gly Gly Glu Ile Tyr Val
        515                 520                 525

Pro Glu Ser Tyr Ala Ala Gln Lys
        530                 535
```

<210> SEQ ID NO 33
<211> LENGTH: 2566
<212> TYPE: DNA
<213> ORGANISM: Oryza sativa

<400> SEQUENCE: 33

```
ttcggcacga ggttctaacc gagttcctca cttcctcctc cgcccgcgtc gcccctcctc    60
tcctctccct cccggctccc ggctaccgcc gccgccgccc cgaggaaatg ctgccctgc    120
aaccctcatt ctcttcagtc cctattggga cggtgcctat taccaagca cttgagaaag    180
ttaatggtat tgctgaaaat ctaagctggg aagtctttag atactttta atcgaacaag    240
ctgagcaggg tgttgattac ttcacaatcc atgctggcgt gcttcttcgt tacattcctc    300
ttacggcaaa gagaatgacc ggcatagttt cacgtggtgg ctctatccat gcaaaatggt    360
gcctaacata tcataaggag aactttgcct atgagcactg ggatgaaatt cttgatattt    420
gcaatcagta tgatgtggca ttatccattg gcgatggttt gagaccaggt tctatttatg    480
atgcaaatga tagtgctcag tttgcagaat tgctgactca aggggaactc acacgccgag    540
cttgggcaaa agatgtgcag gtaatgaatg aaggcccagg gcacattccg atgcataaaa    600
ttcctgaaaa catggagaag caactggagt ggtgcaatga agcacctttc tacacactgg    660
ggccactgac aactgatatt gcacctggtt atgatcacat cacctccgcc attggtgctg    720
ccaacattgg ggctcttggc actgcacttc tctgttatgt aacaccaaag gagcaccttg    780
gattgcctaa ccgtgatgat gttaagacag gcgtgatatc ctacaaaatt tctgctcatg    840
ctgctgattt ggcaaagggc catccctatg cacaagcatg gacgatacac taagcaagg    900
caagatttga gtttagatgg ttggatcaat ttgctctatc tctggatcct gtgaccgcta    960
```

-continued

```
tgtctttcca tgatgaaaca ttaccatcgg agggtgccaa agtggcacat ttctgctcaa      1020
tgtgtggccc aaagttttgt tcgatgaaaa tcacagagga tattagaaaa tatgctgatg      1080
aacatggtta cgggacagtg gaggaagcgg tgatacaagg aatgaatgct atgagtgctg      1140
agttttcagc tgcaaggaaa acaatcagtg gggagcaaca tggtgaagct ggaggggaga      1200
tatatgttcc agaaagctat acagctcgca ataagatcg tcttggtgtc catctactcc       1260
gggtggagcg tttatcagca gcactcctca ccatcctatg ttaggaggtg gggtgcctgt      1320
attctcaacg atctgaaggc tcttggcct ggattgttgt gaattgggct gagaaagtcc       1380
ctttgaacct gaacaggata atgcctgcga agggagtgtg catttctact tttatgtttc      1440
cagggaactc tcaacacaac ccctttttgg tgggagatcg agctatccaa tatgttcctg      1500
aacgtgtgag ctcagcagct ggatatacct gtttcttaca actgaggtaa catggtaata      1560
atacttcatt tgataagtgg catgctgaca tttctccaac aggagaggat ttctgcagat      1620
accacttcgt aatgtcccag aactgattta gtcatacatt tattatccgt gtaaatttgc      1680
aaagcgttgg ccatgtccta tgcaattgat tttaaaccat ctatctgcac atatctaatt     1740
aaagtataaa acaatttata aactctacat aatggacatt ttagctgcat gccacttgtc     1800
aattgagcac acaatatact gactaaattc aatttaactt gatcatgatt catgtggaag     1860
gtgtttatta ggaattaatt tattgatatg gccagagact tgtttatttt tagctattta    1920
tttgtctttc ccatagaaat gatcaaattt tgtacttaca ccttgtgtaa gtataatgaa    1980
attatttagt ctgttttgga gcattcatta atgcaatgat gctcagccgc tcagatcttt    2040
gcgtagcatt atccaagaaa acaagtcttt ttgtatcccc tagataattt gaaagcaccc    2100
atacatgcac aatagcatgt gaaaagaac tttagctagg ttctgttgac cgattatgtt     2160
gtaggatagg aatcatctgc ctgtagaaca taatttgggc attatcttct gatgttataa    2220
tcatgttttt ctcagcaaac tattactccg cactccattt tgtgtttgcg atgtggaatt    2280
attttacctg tgatccaatc ccattatttg actgacgtga aacgttaagt gaaatgacgt    2340
gtggacaaag ttgctcgtgg ctggagtctt tatgctcgtg gttaacaatt tggagatgaa    2400
ttttgctctg attgtgctcc tgcaatgtgt ttttaatttt catcataacg gatcttgaca    2460
ctattttcta tcagattgtt acctgttgtt cattccgagt tcagtactac tatacaatgt    2520
ccgatcaagt tcagatatta aaaaaaaaaa aaaaaaaaaa aaaaaa                   2566
```

<210> SEQ ID NO 34
<211> LENGTH: 410
<212> TYPE: PRT
<213> ORGANISM: Oryza sativa

<400> SEQUENCE: 34

```
Arg His Glu Val Leu Thr Glu Phe Leu Thr Ser Ser Ser Ala Arg Val
 1               5                   10                  15

Ala Pro Pro Leu Leu Ser Leu Pro Ala Pro Gly Tyr Arg Arg Arg Arg
                20                  25                  30

Pro Glu Glu Met Ala Ala Leu Gln Pro Ser Phe Ser Ser Val Pro Ile
            35                  40                  45

Gly Thr Val Pro Ile Tyr Gln Ala Leu Glu Lys Val Asn Gly Ile Ala
        50                  55                  60

Glu Asn Leu Ser Trp Glu Val Phe Arg Asp Thr Leu Ile Glu Gln Ala
 65                  70                  75                  80

Glu Gln Gly Val Asp Tyr Phe Thr Ile His Ala Gly Val Leu Leu Arg
                85                  90                  95
```

```
Tyr Ile Pro Leu Thr Ala Lys Arg Met Thr Gly Ile Val Ser Arg Gly
            100                 105                 110

Gly Ser Ile His Ala Lys Trp Cys Leu Thr Tyr His Lys Glu Asn Phe
        115                 120                 125

Ala Tyr Glu His Trp Asp Glu Ile Leu Asp Ile Cys Asn Gln Tyr Asp
    130                 135                 140

Val Ala Leu Ser Ile Gly Asp Gly Leu Arg Pro Gly Ser Ile Tyr Asp
145                 150                 155                 160

Ala Asn Asp Ser Ala Gln Phe Ala Glu Leu Leu Thr Gln Gly Glu Leu
                165                 170                 175

Thr Arg Arg Ala Trp Ala Lys Asp Val Gln Val Met Asn Glu Gly Pro
            180                 185                 190

Gly His Ile Pro Met His Lys Ile Pro Glu Asn Met Glu Lys Gln Leu
        195                 200                 205

Glu Trp Cys Asn Glu Ala Pro Phe Tyr Thr Leu Gly Pro Leu Thr Thr
    210                 215                 220

Asp Ile Ala Pro Gly Tyr Asp His Ile Thr Ser Ala Ile Gly Ala Ala
225                 230                 235                 240

Asn Ile Gly Ala Leu Gly Thr Ala Leu Leu Cys Tyr Val Thr Pro Lys
                245                 250                 255

Glu His Leu Gly Leu Pro Asn Arg Asp Asp Val Lys Thr Gly Val Ile
            260                 265                 270

Ser Tyr Lys Ile Ser Ala His Ala Ala Asp Leu Ala Lys Gly His Pro
        275                 280                 285

Tyr Ala Gln Ala Trp Asp Asp Thr Leu Ser Lys Ala Arg Phe Glu Phe
    290                 295                 300

Arg Trp Leu Asp Gln Phe Ala Leu Ser Leu Asp Pro Val Thr Ala Met
305                 310                 315                 320

Ser Phe His Asp Glu Thr Leu Pro Ser Glu Gly Ala Lys Val Ala His
                325                 330                 335

Phe Cys Ser Met Cys Gly Pro Lys Phe Cys Ser Met Lys Ile Thr Glu
            340                 345                 350

Asp Ile Arg Lys Tyr Ala Asp Glu His Gly Tyr Gly Thr Val Glu Glu
        355                 360                 365

Ala Val Ile Gln Gly Met Asn Ala Met Ser Ala Glu Phe Ser Ala Ala
    370                 375                 380

Arg Lys Thr Ile Ser Gly Glu Gln His Gly Glu Ala Gly Gly Glu Ile
385                 390                 395                 400

Tyr Val Pro Glu Ser Tyr Thr Ala Arg Lys
                405                 410

<210> SEQ ID NO 35
<211> LENGTH: 1256
<212> TYPE: DNA
<213> ORGANISM: Glycine max

<400> SEQUENCE: 35
gcacgagggg acaccctgat tgaacaagct gagcagggtg tggattactt caccatccat      60
gcaggagttc ttctgagata cgttccatta acggctaagc gcatgacagg aatagtctca     120
agaggagggt ctattcatgc aaagtggtgc ttagcttatc acaaagagaa ttttgcttat     180
gagcactggg atgagatact tgacatctgc aatcagtatg atgtggccct atccattggt     240
gatgggctaa gacctggatc catctatgat gcaaatgaca cagctcagtt cgccgaactc     300
```

-continued

```
ttgacacaag gagaattgac ccgtagagca tgggagaagg atgtacaggt gatgaatgaa    360
ggacctggac atgtcccaat gcacaagatt cctgaaaaca tgcagaaaca gttagaatgg    420
tgtagtgaag cgcctttta cactcttggt cctttgacta ctgatattgc ccctggctat     480
gatcacatca cctctgcaat tggtgctgca aatattgggg cacttggtac agctcttctc    540
tgttatgtga ctccaaaaga acatcttggg ttgccaaacc gggatgacgt gaaggctggc    600
gttatagctt acaagattgc ggctcatgct gctgatttag ccaaaggcca tccatatgct    660
caagcttggg atgatgaatt gagcaaggca agatttgagt ccgatggat ggaccagttt     720
gctttgtcat tggatccgat gacagccacg tccttccatg acgaaaccct accggcagat    780
ggtgcgaaag tggcccattt ctgctcaatg tgtggcccta aattctgctc tatgaagatt    840
acagaggatg tgaggaagta tgctgcggaa catggctatg aactgatga agctttgcag     900
cgtgggatgg atgctatgag tgctgaattt caagctgcca agaagaccat cagtggggag    960
caacatggtg aagctggtgg agagatttac ttgccagaag cttacgttag aaccaagagg    1020
actacttaat ggagcaaatc agttggaaga acttgtagct agcttcccaa ctggcttatc    1080
tgagtgtgga gaagcattat caagccttag gagtaggaga acgagtactg tttgtgatga    1140
atgtctatgg tttaagaaat ctgtctttag tcaacttgtg tgttttgtta ttcagttctc    1200
agcaataaac tgctctggca atctagtttc aaaaaaaaaa aaaaaaaaaa aaaaaa        1256
```

<210> SEQ ID NO 36
<211> LENGTH: 342
<212> TYPE: PRT
<213> ORGANISM: Glycine max

<400> SEQUENCE: 36

```
Ala Arg Gly Asp Thr Leu Ile Glu Gln Ala Glu Gln Gly Val Asp Tyr
  1               5                  10                  15

Phe Thr Ile His Ala Gly Val Leu Leu Arg Tyr Val Pro Leu Thr Ala
                 20                  25                  30

Lys Arg Met Thr Gly Ile Val Ser Arg Gly Gly Ser Ile His Ala Lys
             35                  40                  45

Trp Cys Leu Ala Tyr His Lys Glu Asn Phe Ala Tyr Glu His Trp Asp
         50                  55                  60

Glu Ile Leu Asp Ile Cys Asn Gln Tyr Asp Val Ala Leu Ser Ile Gly
 65                  70                  75                  80

Asp Gly Leu Arg Pro Gly Ser Ile Tyr Asp Ala Asn Asp Thr Ala Gln
                 85                  90                  95

Phe Ala Glu Leu Leu Thr Gln Gly Glu Leu Thr Arg Arg Ala Trp Glu
            100                 105                 110

Lys Asp Val Gln Val Met Asn Glu Gly Pro Gly His Val Pro Met His
            115                 120                 125

Lys Ile Pro Glu Asn Met Gln Lys Gln Leu Glu Trp Cys Ser Glu Ala
        130                 135                 140

Pro Phe Tyr Thr Leu Gly Pro Leu Thr Thr Asp Ile Ala Pro Gly Tyr
145                 150                 155                 160

Asp His Ile Thr Ser Ala Ile Gly Ala Ala Asn Ile Gly Ala Leu Gly
                165                 170                 175

Thr Ala Leu Leu Cys Tyr Val Thr Pro Lys Glu His Leu Gly Leu Pro
            180                 185                 190

Asn Arg Asp Asp Val Lys Ala Gly Val Ile Ala Tyr Lys Ile Ala Ala
            195                 200                 205
```

```
His Ala Asp Leu Ala Lys Gly His Pro Tyr Ala Gln Ala Trp Asp
    210                 215                 220
Asp Glu Leu Ser Lys Ala Arg Phe Glu Phe Arg Trp Met Asp Gln Phe
225                 230                 235                 240
Ala Leu Ser Leu Asp Pro Met Thr Ala Thr Ser Phe His Asp Glu Thr
                245                 250                 255
Leu Pro Ala Asp Gly Ala Lys Val Ala His Phe Cys Ser Met Cys Gly
            260                 265                 270
Pro Lys Phe Cys Ser Met Lys Ile Thr Glu Asp Val Arg Lys Tyr Ala
        275                 280                 285
Ala Glu His Gly Tyr Gly Thr Asp Glu Ala Leu Gln Arg Gly Met Asp
    290                 295                 300
Ala Met Ser Ala Glu Phe Gln Ala Ala Lys Lys Thr Ile Ser Gly Glu
305                 310                 315                 320
Gln His Gly Glu Ala Gly Gly Glu Ile Tyr Leu Pro Glu Ala Tyr Val
                325                 330                 335
Arg Thr Lys Arg Thr Thr
                340

<210> SEQ ID NO 37
<211> LENGTH: 2406
<212> TYPE: DNA
<213> ORGANISM: Triticum aestivum

<400> SEQUENCE: 37
gcacgagacg aaacacacag ttgatcctgc tgctcccgaa tttctgccgc tcccagcatt     60
tgaagactgc ttcccacgga gcaccaaaga atgcagtgaa gtcgttcatg aggaaacagg    120
tcatgccctg aaggttccat ttcggagagt ccatttgacc ggagatagcg ggcatttcga    180
cacatatgac accagtggtc cacaaaacat aagcccaagg ctcggactcc aaagataag    240 aaaggaatgg attgacagga gagagaagtt gggtagtcct cgttacacgc aaatgtacta    300
tgctaagcag ggaatcataa cagaggagat actgtactgt gccaaacgcg agaaccttgc    360
tcctgaattt gtccggtcag aagtcgcccg tggacgagcc attatccctt ccaacaagag    420
gcacctggaa ttggaaccca tgattgttgg aagaaacttc cttgtaaagg tgaatgctaa    480
cattgggaac tctgctgttg tgagctccat tgaggaggaa gtccacaagc tccagtgggc    540
cacaatgtgg ggagcagata ctgtcatgga cctttcaaca gggcgccata tccatgagac    600
ccgggaatgg attattcgta actcttcggt tcctattgga actgttccta tttaccaagc    660
acttgagaaa gttaacggta ttgctgaaga tctgagctgg gaagtcttta gggacacttt    720
aattgaacaa gccgagcagg gtgttgatta cttcaccatc cacgctggtg tgctgcttcg    780
atatattcct ctcacagcaa agagaatgac cggcatagtt tctcgtggtg gatcaatcca    840
tgcaaaatgg tgcttgacgt atcacaagga gaactttgct tatgagcact gggatgacat    900
tcttgacata tgtaaccagt atgatgtggc attatctatt ggtgatggcc tgaggcctgg    960
ttccatttat gatgctaatg atagtgctca gtttgcagaa ctgctgactc agggggaact   1020
aactcgccga gcatgggaga agatgtgca ggtgatgaat gaaggtcctg gcatattcc    1080 gatgcataag attcctgaaa atatggagaa acagctggag tggtgcaacg aagcaccttt   1140
ctatacgttg ggtccattga ccactgatat tgcacctggt tatgatcaca tcacctcagc   1200
cattggtgct gccaacattg gggctcttgg cactgcactt ctttgttatg taacaccaaa   1260
ggagcacctt gggttgccta acagggatga tgttaagaca ggtgtgatat cctacaaaat   1320
```

-continued

```
cgctgctcat gctgctgatt tggcaaagcg tcacccctat gcacaagcat gggatgatgc      1380
actaagcaag gcaaggtttg agtttagatg gttggaccaa tttgctttat ccctggatcc      1440
agttactgca atgtctttcc atgatgaaac actgccgtct gatggcgcca agtagcaca       1500 tttctgctca atgtgtggtc ccaagttttg ctcgatgaaa atcaccgagg atattagaaa      1560
gtatgctgat gaacatggtt acgggacagt agaggaagcg gtgagacaag gaatgagtga      1620
gatgagtgct gaatttttgg ctgcaagaaa aacaattagt ggcgaacaac atggtgaagc      1680
tggaggggaa atctatgtgc cagaaagcta cgtagttcag aaataagatg tccttggcag      1740
ccgtctgatc caagtgatgc agatttggtg gctaggtcgt ttgtcagcag cacttctacc      1800
atcttctgtt aggaggtgac cccttggcct ggattgttgc gatatgggct gagaaagtcc      1860
ctttgaacct gaacaggata atgcctgcga agggagtgtg catttttatt ttcatgtttc      1920
ccaggataca ctcaaccctc gacattctgg aaatcgaggg accaagttt cctgaatgtg       1980 tggagcgcat ctactggata tgcatgtttc ctactctgaa gtaacatggt aatgtacacg      2040
atttcttgaa ccagcataca tattggtatt tctccaagag gagagaatat ttacaggcat      2100
agtgttacca tggaacacat aaaatttagt caacatggaa cacataaaat ttagtcatac      2160
gtgtggctag tttagtcaaa cttcataagc ccataatttt tttgaggaat cccattacat      2220
ctcgcaaagc attcacaatg tcctgtgtaa tttactttt acacctatcc ttgtacatat       2280
ttctatataa gtagaatata aagatgtaa ctagattgac agaaaaaaaa aaaaaaaaa        2340 aaaaaaaaaa agcaaaaaaa aaaaaaaaaa aaaaaaaaaa aaaaaaaaaa aaaaaaaaaa      2400
aaaaaa                                                                2406
```

<210> SEQ ID NO 38
<211> LENGTH: 574
<212> TYPE: PRT
<213> ORGANISM: Triticum aestivum

<400> SEQUENCE: 38

```
His Glu Thr Lys His Thr Val Asp Pro Ala Ala Pro Glu Phe Leu Pro
  1               5                  10                  15

Leu Pro Ala Phe Glu Asp Cys Phe Pro Arg Ser Thr Lys Glu Cys Ser
                 20                  25                  30

Glu Val His Glu Glu Thr Gly His Ala Leu Lys Val Pro Phe Arg
             35                  40                  45

Arg Val His Leu Thr Gly Asp Ser Gly His Phe Asp Thr Tyr Asp Thr
         50                  55                  60

Ser Gly Pro Gln Asn Ile Ser Pro Arg Leu Gly Leu Pro Lys Ile Arg
 65                  70                  75                  80

Lys Glu Trp Ile Asp Arg Arg Glu Lys Leu Gly Ser Pro Arg Tyr Thr
                 85                  90                  95

Gln Met Tyr Tyr Ala Lys Gln Gly Ile Ile Thr Glu Ile Leu Tyr
                100                 105                 110

Cys Ala Lys Arg Glu Asn Leu Ala Pro Glu Phe Val Arg Ser Glu Val
            115                 120                 125

Ala Arg Gly Arg Ala Ile Ile Pro Ser Asn Lys Arg His Leu Glu Leu
        130                 135                 140

Glu Pro Met Ile Val Gly Arg Asn Phe Leu Val Lys Val Asn Ala Asn
145                 150                 155                 160

Ile Gly Asn Ser Ala Val Val Ser Ile Glu Glu Val His Lys
                165                 170                 175
```

```
Leu Gln Trp Ala Thr Met Trp Gly Ala Asp Thr Val Met Asp Leu Ser
            180                 185                 190

Thr Gly Arg His Ile His Glu Thr Arg Glu Trp Ile Ile Arg Asn Ser
            195                 200                 205

Ser Val Pro Ile Gly Thr Val Pro Ile Tyr Gln Ala Leu Glu Lys Val
            210                 215                 220

Asn Gly Ile Ala Glu Asp Leu Ser Trp Glu Val Phe Arg Asp Thr Leu
225                 230                 235                 240

Ile Glu Gln Ala Glu Gln Gly Val Asp Tyr Phe Thr Ile His Ala Gly
                    245                 250                 255

Val Leu Arg Tyr Ile Pro Leu Thr Ala Lys Arg Met Thr Gly Ile
            260                 265                 270

Val Ser Arg Gly Gly Ser Ile His Ala Lys Trp Cys Leu Thr Tyr His
            275                 280                 285

Lys Glu Asn Phe Ala Tyr Glu His Trp Asp Asp Ile Leu Asp Ile Cys
            290                 295                 300

Asn Gln Tyr Asp Val Ala Leu Ser Ile Gly Asp Gly Leu Arg Pro Gly
305                 310                 315                 320

Ser Ile Tyr Asp Ala Asn Asp Ser Ala Gln Phe Ala Glu Leu Leu Thr
                    325                 330                 335

Gln Gly Glu Leu Thr Arg Arg Ala Trp Glu Lys Asp Val Gln Val Met
            340                 345                 350

Asn Glu Gly Pro Gly His Ile Pro Met His Lys Ile Pro Glu Asn Met
            355                 360                 365

Glu Lys Gln Leu Glu Trp Cys Asn Glu Ala Pro Phe Tyr Thr Leu Gly
            370                 375                 380

Pro Leu Thr Thr Asp Ile Ala Pro Gly Tyr Asp His Ile Thr Ser Ala
385                 390                 395                 400

Ile Gly Ala Ala Asn Ile Gly Ala Leu Gly Thr Ala Leu Leu Cys Tyr
                    405                 410                 415

Val Thr Pro Lys Glu His Leu Gly Leu Pro Asn Arg Asp Asp Val Lys
            420                 425                 430

Thr Gly Val Ile Ser Tyr Lys Ile Ala Ala His Ala Ala Asp Leu Ala
            435                 440                 445

Lys Arg His Pro Tyr Ala Gln Ala Trp Asp Asp Ala Leu Ser Lys Ala
            450                 455                 460

Arg Phe Glu Phe Arg Trp Leu Asp Gln Phe Ala Leu Ser Leu Asp Pro
465                 470                 475                 480

Val Thr Ala Met Ser Phe His Asp Glu Thr Leu Pro Ser Asp Gly Ala
                    485                 490                 495

Lys Val Ala His Phe Cys Ser Met Cys Gly Pro Lys Phe Cys Ser Met
            500                 505                 510

Lys Ile Thr Glu Asp Ile Arg Lys Tyr Ala Asp Glu His Gly Tyr Gly
            515                 520                 525

Thr Val Glu Glu Ala Val Arg Gln Gly Met Ser Glu Met Ser Ala Glu
            530                 535                 540

Phe Leu Ala Ala Arg Lys Thr Ile Ser Gly Glu Gln His Gly Glu Ala
545                 550                 555                 560

Gly Gly Glu Ile Tyr Val Pro Glu Ser Tyr Val Val Gln Lys
                    565                 570

<210> SEQ ID NO 39
<211> LENGTH: 354
<212> TYPE: PRT
```

<213> ORGANISM: maize

<400> SEQUENCE: 39

```
Met Ala Thr Ala Ala Ser Ser Leu Leu Lys Ser Ser Phe Ala Gly
  1               5                  10                  15

Ser Arg Leu Pro Ala Ala Thr Arg Thr Thr Pro Ala Ser Leu Val Val
             20                  25                  30

Ala Thr Gly Pro Arg Gly Ala Gly Ala Gly Pro Ile Cys Ala Ser Met
         35                  40                  45

Ser Met Ser Ser Ser Asn Pro Pro Tyr Asp Leu Thr Ser Phe Arg Phe
     50                  55                  60

Ser Pro Ile Lys Glu Ser Ile Val Ser Arg Glu Met Thr Arg Arg Tyr
 65                  70                  75                  80

Met Thr Asp Met Ile Thr Tyr Ala Asp Thr Asp Val Val Ile Val Gly
                 85                  90                  95

Ala Gly Ser Ala Gly Leu Ser Cys Ala Tyr Glu Leu Ser Lys Asp Pro
             100                 105                 110

Ala Val Ser Ile Ala Ile Val Glu Gln Ser Val Ser Pro Gly Gly Gly
             115                 120                 125

Ala Trp Leu Gly Gly Gln Leu Phe Ser Ala Met Val Val Arg Lys Pro
 130                 135                 140

Ala His Leu Phe Leu Asp Glu Leu Gly Val Ala Tyr Asp Glu Ala Glu
145                 150                 155                 160

Asp Tyr Val Val Ile Lys His Ala Ala Leu Phe Thr Ser Thr Val Met
                 165                 170                 175

Ser Leu Leu Leu Ala Arg Pro Asn Val Lys Leu Phe Asn Ala Val Ala
             180                 185                 190

Val Glu Asp Leu Ile Val Arg Gly Gly Arg Val Gly Gly Val Val Thr
             195                 200                 205

Asn Trp Ala Leu Val Ser Met Asn His Asp Thr Gln Ser Cys Met Asp
 210                 215                 220

Pro Asn Val Met Glu Ala Lys Val Val Ser Ser Cys Gly His Asp
225                 230                 235                 240

Gly Pro Phe Gly Ala Thr Gly Val Lys Arg Leu Gln Asp Ile Gly Met
                 245                 250                 255

Ile Ser Ala Val Pro Gly Met Lys Ala Leu Asp Met Asn Thr Ala Glu
             260                 265                 270

Asp Glu Ile Val Arg Leu Thr Arg Glu Val Val Pro Gly Met Ile Val
             275                 280                 285

Thr Gly Met Glu Val Ala Glu Ile Asp Gly Ala Pro Arg Met Gly Pro
 290                 295                 300

Thr Phe Gly Ala Met Met Ile Ser Gly Gln Lys Ala Ala His Leu Ala
305                 310                 315                 320

Leu Lys Ala Leu Gly Arg Pro Asn Ala Val Asp Gly Thr Met Ser Pro
                 325                 330                 335

Pro Leu Arg Glu Glu Leu Met Ile Ala Tyr Lys Asp Asp Glu Val Val
             340                 345                 350

Asp Ala
```

<210> SEQ ID NO 40
<211> LENGTH: 354
<212> TYPE: PRT
<213> ORGANISM: Zea mays

<400> SEQUENCE: 40

```
Met Ala Thr Thr Ala Ala Ser Ser Leu Leu Lys Ser Ser Phe Ala Gly
 1               5                  10                  15

Ser Arg Leu Pro Ser Ala Thr Arg Thr Thr Pro Ser Ser Val Ala
            20                  25                  30

Val Ala Thr Pro Arg Ala Gly Gly Pro Ile Arg Ala Ser Ile Ser
        35                  40                  45

Ser Pro Asn Pro Pro Tyr Asp Leu Thr Ser Phe Arg Phe Ser Pro Ile
    50                  55                  60

Lys Glu Ser Ile Val Ser Arg Glu Met Thr Arg Arg Tyr Met Thr Asp
 65                  70                  75                  80

Met Ile Thr His Ala Asp Thr Asp Val Val Ile Val Gly Ala Gly Ser
                85                  90                  95

Ala Gly Leu Ser Cys Ala Tyr Glu Leu Ser Lys Asp Pro Thr Val Ser
                100                 105                 110

Val Ala Ile Val Glu Gln Ser Val Ser Pro Gly Gly Gly Ala Trp Leu
                115                 120                 125

Gly Gly Gln Leu Phe Ser Ala Met Val Val Arg Arg Pro Ala His Leu
            130                 135                 140

Phe Leu Asp Glu Leu Gly Val Gly Tyr Asp Glu Ala Glu Asp Tyr Val
145                 150                 155                 160

Val Val Lys His Ala Ala Leu Phe Thr Ser Thr Val Met Ser Arg Leu
                165                 170                 175

Leu Ala Arg Pro Asn Val Lys Leu Phe Asn Ala Val Ala Val Glu Asp
                180                 185                 190

Leu Ile Val Arg Arg Gly Arg Val Gly Gly Val Val Thr Asn Trp Ala
                195                 200                 205

Leu Val Ser Met Asn His Asp Thr Gln Ser Cys Met Asp Pro Asn Val
            210                 215                 220

Met Glu Ala Lys Val Val Ser Ser Cys Gly His Asp Gly Pro Phe
225                 230                 235                 240

Gly Ala Thr Gly Val Lys Arg Leu Gln Asp Ile Gly Met Ile Ser Ala
                245                 250                 255

Val Pro Gly Met Lys Ala Leu Asp Met Asn Ala Ala Glu Asp Glu Ile
                260                 265                 270

Val Arg Leu Thr Arg Glu Val Val Pro Gly Met Ile Val Thr Gly Met
            275                 280                 285

Glu Val Ala Glu Ile Asp Gly Ala Pro Arg Met Gly Pro Thr Phe Gly
            290                 295                 300

Ala Met Met Ile Ser Gly Gln Lys Ala Ala His Leu Ala Leu Lys Ala
305                 310                 315                 320

Leu Gly Arg Pro Asn Ala Val Asp Gly Thr Ile Pro Glu Val Ser Pro
                325                 330                 335

Ala Leu Arg Glu Glu Phe Val Ile Ala Ser Lys Asp Asp Glu Val Val
                340                 345                 350

Asp Ala
```

<210> SEQ ID NO 41
<211> LENGTH: 590
<212> TYPE: PRT
<213> ORGANISM: Bacillus subtilis

<400> SEQUENCE: 41

```
Met Gln Asn Asn Ser Val Gln Gln Ala Asn Ile Ser Ile Met Ser Ser
 1               5                  10                  15
```

```
Phe Ser Gly Ser Lys Lys Val Tyr Val Glu Gly Ser Ser Asp Ile
                20                  25                  30
Gln Val Pro Met Arg Glu Ile Ala Leu Ser Pro Thr Thr Gly Ser Phe
            35                  40                  45
Gly Glu Glu Glu Asn Ala Pro Val Arg Val Tyr Asp Thr Ser Gly Pro
        50                  55                  60
Tyr Thr Asp Pro Glu Val Thr Ile Asn Ile Gln Glu Gly Leu Lys Pro
 65                 70                  75                  80
Leu Arg Gln Ile Trp Ile Thr Glu Arg Gly Asp Val Glu Glu Tyr Glu
                85                  90                  95
Gly Arg Ala Ile Lys Pro Glu Asp Asn Gly Tyr Lys Lys Ala Lys Pro
            100                 105                 110
Asn Val Ser Tyr Pro Gly Leu Lys Arg Lys Pro Leu Arg Ala Lys Ala
        115                 120                 125
Gly Gln Asn Val Thr Gln Met His Tyr Ala Lys Lys Gly Ile Ile Thr
        130                 135                 140
Pro Glu Met Glu Phe Ile Ala Ile Arg Glu His Val Ser Pro Glu Phe
145                 150                 155                 160
Val Arg Asp Glu Val Ala Ser Gly Arg Ala Ile Ile Pro Ser Asn Ile
                165                 170                 175
Asn His Pro Glu Ser Glu Pro Met Ile Ile Gly Arg Asn Phe His Val
            180                 185                 190
Lys Ile Asn Ala Asn Ile Gly Asn Ser Ala Val Thr Ser Ser Ile Glu
        195                 200                 205
Glu Glu Val Glu Lys Met Thr Trp Ala Ile Arg Trp Gly Ala Asp Thr
        210                 215                 220
Met Met Asp Leu Ser Thr Gly Lys Asp Ile His Thr Thr Arg Glu Trp
225                 230                 235                 240
Ile Ile Arg Asn Cys Pro Val Pro Val Gly Thr Val Pro Ile Tyr Gln
                245                 250                 255
Ala Leu Glu Lys Val Asn Gly Val Ala Glu Asp Leu Thr Trp Glu Ile
            260                 265                 270
Tyr Arg Asp Thr Leu Ile Glu Gln Ala Glu Gln Gly Val Asp Tyr Phe
        275                 280                 285
Thr Ile His Ala Gly Val Leu Leu Arg Tyr Val Pro Leu Thr Ala Lys
        290                 295                 300
Arg Thr Thr Gly Ile Val Ser Arg Gly Gly Ala Ile Met Ala Gln Trp
305                 310                 315                 320
Cys Leu Ala His His Gln Glu Ser Phe Leu Tyr Thr His Phe Glu Glu
                325                 330                 335
Ile Cys Glu Ile Met Lys Met Tyr Asp Ile Ala Phe Ser Leu Gly Asp
            340                 345                 350
Gly Leu Arg Pro Gly Ser Ile Ala Asp Ala Asn Asp Glu Ala Gln Phe
        355                 360                 365
Ala Glu Leu Glu Thr Leu Gly Glu Leu Thr Gln Ile Ala Trp Lys His
        370                 375                 380
Asp Val Gln Val Met Ile Glu Gly Pro Gly His Val Pro Met His Lys
385                 390                 395                 400
Ile Lys Glu Asn Val Asp Lys Gln Met Asp Ile Cys Lys Glu Ala Pro
                405                 410                 415
Phe Tyr Thr Leu Gly Pro Leu Thr Thr Asp Ile Ala Pro Gly Tyr Asp
            420                 425                 430
```

```
His Ile Thr Ser Ala Ile Gly Ala Ala Met Ile Gly Trp Tyr Gly Thr
            435                 440                 445

Ala Met Leu Cys Tyr Val Thr Pro Lys Glu His Leu Gly Leu Pro Asn
    450                 455                 460

Arg Asp Asp Val Arg Glu Gly Val Ile Thr Tyr Lys Ile Ala Ala His
465                 470                 475                 480

Ala Ala Asp Leu Ala Lys Gly His Pro Gly Ala Gln Ile Arg Asp Asp
                485                 490                 495

Ala Leu Ser Lys Ala Arg Phe Glu Phe Arg Trp Arg Asp Gln Phe Asn
            500                 505                 510

Leu Ser Leu Asp Pro Glu Arg Ala Leu Glu Tyr His Asp Glu Thr Leu
        515                 520                 525

Pro Ala Glu Gly Ala Lys Thr Ala His Phe Cys Ser Met Cys Gly Pro
    530                 535                 540

Lys Phe Cys Ser Met Arg Ile Ser Gln Asp Ile Arg Asp Tyr Ala Lys
545                 550                 555                 560

Lys Asn Asp Leu Ser Glu Ala Glu Ala Ile Asn Lys Gly Leu Lys Glu
                565                 570                 575

Lys Ala Lys Glu Phe Val Asp Thr Gly Ser Asn Leu Tyr Gln
            580                 585                 590

<210> SEQ ID NO 42
<211> LENGTH: 644
<212> TYPE: PRT
<213> ORGANISM: Arabidopsis thaliana

<400> SEQUENCE: 42

Met Ala Ala Ser Val His Cys Thr Leu Met Ser Val Val Cys Asn Asn
  1               5                  10                  15

Lys Asn His Ser Ala Arg Pro Lys Leu Pro Asn Ser Ser Leu Leu Pro
                20                  25                  30

Gly Phe Asp Val Val Gln Ala Ala Thr Arg Phe Lys Lys Glu
             35                  40                  45

Thr Thr Thr Thr Arg Ala Thr Leu Thr Phe Asp Pro Pro Thr Thr Asn
     50                  55                  60

Ser Glu Arg Ala Lys Gln Arg Lys His Thr Ile Asp Pro Ser Ser Pro
 65                  70                  75                  80

Asp Phe Gln Pro Ile Pro Ser Phe Glu Glu Cys Phe Pro Lys Ser Thr
                 85                  90                  95

Lys Glu His Lys Glu Val Val His Glu Glu Ser Gly His Val Leu Lys
            100                 105                 110

Val Pro Phe Arg Arg Val His Leu Ser Gly Gly Glu Pro Ala Phe Asp
        115                 120                 125

Asn Tyr Asp Thr Ser Gly Pro Gln Asn Val Asn Ala His Ile Gly Leu
    130                 135                 140

Ala Lys Leu Arg Lys Glu Trp Ile Asp Arg Arg Glu Lys Leu Gly Thr
145                 150                 155                 160

Pro Arg Tyr Thr Gln Met Tyr Tyr Ala Lys Gln Gly Ile Ile Thr Glu
                165                 170                 175

Glu Met Leu Tyr Cys Ala Thr Arg Glu Lys Leu Asp Pro Glu Phe Val
            180                 185                 190

Arg Ser Glu Val Ala Arg Gly Arg Ala Ile Ile Pro Ser Asn Lys Lys
        195                 200                 205

His Leu Glu Leu Glu Pro Met Ile Val Gly Arg Lys Phe Leu Val Lys
    210                 215                 220
```

```
Val Asn Ala Asn Ile Gly Asn Ser Ala Val Ala Ser Ser Ile Glu Glu
225                 230                 235                 240

Glu Val Tyr Lys Val Gln Trp Ala Thr Met Trp Gly Ala Asp Thr Ile
            245                 250                 255

Met Asp Leu Ser Thr Gly Arg His Ile His Glu Thr Arg Glu Trp Ile
            260                 265                 270

Leu Arg Asn Ser Ala Val Pro Val Gly Thr Val Pro Ile Tyr Gln Ala
        275                 280                 285

Leu Glu Lys Val Asp Gly Ile Ala Glu Asn Leu Asn Trp Glu Val Phe
    290                 295                 300

Arg Glu Thr Leu Ile Glu Gln Ala Glu Gln Gly Val Asp Tyr Phe Thr
305                 310                 315                 320

Ile His Ala Gly Val Leu Leu Arg Tyr Ile Pro Leu Thr Ala Lys Arg
                325                 330                 335

Leu Thr Gly Ile Val Ser Arg Gly Gly Ser Ile His Ala Lys Trp Cys
            340                 345                 350

Leu Ala Tyr His Lys Glu Asn Phe Ala Tyr Glu His Trp Asp Asp Ile
        355                 360                 365

Leu Asp Ile Cys Asn Gln Tyr Asp Val Ala Leu Ser Ile Gly Asp Gly
    370                 375                 380

Leu Arg Pro Gly Ser Ile Tyr Asp Ala Asn Asp Thr Ala Gln Phe Ala
385                 390                 395                 400

Glu Leu Leu Thr Gln Gly Glu Leu Thr Arg Arg Ala Trp Glu Lys Asp
                405                 410                 415

Val Gln Val Met Asn Glu Gly Pro Gly His Val Pro Met His Lys Ile
            420                 425                 430

Pro Glu Asn Met Gln Lys Gln Leu Glu Trp Cys Asn Glu Ala Pro Phe
        435                 440                 445

Tyr Thr Leu Gly Pro Leu Thr Thr Asp Ile Ala Pro Gly Tyr Asp His
    450                 455                 460

Ile Thr Ser Ala Ile Gly Ala Ala Asn Ile Gly Ala Leu Gly Thr Ala
465                 470                 475                 480

Leu Leu Cys Tyr Val Thr Pro Lys Glu His Leu Gly Leu Pro Asn Arg
                485                 490                 495

Asp Asp Val Lys Ala Gly Val Ile Ala Tyr Lys Ile Ala Ala His Ala
            500                 505                 510

Ala Asp Leu Ala Lys Gln His Pro His Ala Gln Ala Trp Asp Asp Ala
        515                 520                 525

Leu Ser Lys Ala Arg Phe Glu Phe Arg Trp Met Asp Gln Phe Ala Leu
    530                 535                 540

Ser Leu Asp Pro Met Thr Ala Met Ser Phe His Asp Glu Thr Leu Pro
545                 550                 555                 560

Ala Asp Gly Ala Lys Val Ala His Phe Cys Ser Met Cys Gly Pro Lys
                565                 570                 575

Phe Cys Ser Met Lys Ile Thr Glu Asp Ile Arg Lys Tyr Ala Glu Glu
            580                 585                 590

Asn Gly Tyr Gly Ser Ala Glu Glu Ala Ile Arg Gln Gly Met Asp Ala
        595                 600                 605

Met Ser Glu Glu Phe Asn Ile Ala Lys Lys Thr Ile Ser Gly Glu Gln
    610                 615                 620

His Gly Glu Val Gly Gly Glu Ile Tyr Leu Pro Glu Ser Tyr Val Lys
625                 630                 635                 640
```

-continued

Ala Ala Gln Lys

<210> SEQ ID NO 43
<211> LENGTH: 1319
<212> TYPE: DNA
<213> ORGANISM: Glycine max

<400> SEQUENCE: 43

```
gcacgaggaa accaaaactg aaaaaaaaaa caaacaatac cataacatgg cttcttccac      60
catcacctcc tccttcctaa catcaccccc ttcatctctc ttcaacaaat catcatcccc     120
ttccttccat gccaccccta ctctccgccc cctcgcgcca cgcgcctcca tgtccgcctc     180
agcgccgccc tacgacttcg gatcgttccg gttcgatccg attagagagt cgattgtgtc     240
gcgcgagatg acccgcaggt acatgatcga catggtcacc cacgccgaca ccgacgtcgt     300
catcgttggc gcgggctccg cgggtctctc gtgcgcctac gagctctcca aaacccctcc     360
atcaacatcg ccattgttga gcagtccgtc cagccccggg ggcggcgcct ggctcggcgg     420
ccaacttttc tccgccatgg tagtgcgtaa gcccgcacac ctcttcctag acgagctcaa     480
tgtggagtat gacgaacaag acaactatgt ggtgatcaag cacgcagcat tgttcacatc     540
caccatcatg agcaagctct tggccaggcc aaacgtgaag ctcttcaatg ccgtggcggc     600
ggaggacttg attgtgaaga acgggagagt tggtggggtg gtgaccaact gggccttggt     660
ttcattgaac catgacactc aatcctgcat ggaccccaat gtgatggagg ctaaggtggt     720
ggtgagttct tgtggccatg atggaccctt tggagccact ggggtgaaga ggctcaagag     780
cattgggtta attgatagtg tgcctgggat gaaggcactt gacatgaaca aggctgagga     840
tgccattgtg aggctcacta gggaggttgt gcctggcatg attgttactg ggatggaagt     900
tgctgagatt gatggtgctc caaggatggg tccaacattt ggagcaatga tgatttcagg     960
gcaaaaagca gcccatctgg ctttgagatc attgggactt cccaatgctt tggattcagt    1020
gggaaacgtt catcctgagc ttgtcctagc tgctgctgaa tccgctgaaa ttgctgaggc    1080
ttaattaatg ttgcaacaaa ttaggttaaa atagtatcaa tgcttgcaac tagaaataat    1140
aattgtagac ttgtacttag ggaattaagc tttgaaggtg ttagtagtga tctattgggg    1200
tggttgatgc gactctatga agtttgttaa tactatatga agctttgagg gtgttgctag    1260
tgatctattg tgtcttactt tcctcgaagc ctaatttaat tgggtctttt ttctattat    1319
```

<210> SEQ ID NO 44
<211> LENGTH: 345
<212> TYPE: PRT
<213> ORGANISM: Glycine max

<400> SEQUENCE: 44

Met Ala Ser Ser Thr Ile Thr Ser Ser Phe Leu Thr Ser Pro Pro Ser
1               5                   10                  15

Ser Leu Phe Asn Lys Ser Ser Pro Ser Phe His Ala Thr Pro Thr
            20                  25                  30

Leu Arg Pro Leu Ala Pro Arg Ala Ser Met Ser Ala Ser Ala Pro Pro
        35                  40                  45

Tyr Asp Phe Gly Ser Phe Arg Phe Asp Pro Ile Arg Glu Ser Ile Val
    50                  55                  60

Ser Arg Glu Met Thr Arg Arg Tyr Met Ile Asp Met Val Thr His Ala
65                  70                  75                  80

Asp Thr Asp Val Val Ile Val Gly Ala Gly Ser Ala Gly Leu Ser Cys
                85                  90                  95

```
Ala Tyr Glu Leu Ser Lys Thr Pro Pro Ser Thr Ser Pro Leu Leu Ser
            100                 105                 110

Ser Pro Ser Ser Pro Gly Gly Gly Ala Trp Leu Gly Gly Gln Leu Phe
        115                 120                 125

Ser Ala Met Val Val Arg Lys Pro Ala His Leu Phe Leu Asp Glu Leu
    130                 135                 140

Asn Val Glu Tyr Asp Glu Gln Asp Asn Tyr Val Val Ile Lys His Ala
145                 150                 155                 160

Ala Leu Phe Thr Ser Thr Ile Met Ser Lys Leu Leu Ala Arg Pro Asn
                165                 170                 175

Val Lys Leu Phe Asn Ala Val Ala Glu Asp Leu Ile Val Lys Asn
            180                 185                 190

Gly Arg Val Gly Gly Val Val Thr Asn Trp Ala Leu Val Ser Leu Asn
        195                 200                 205

His Asp Thr Gln Ser Cys Met Asp Pro Asn Val Met Glu Ala Lys Val
    210                 215                 220

Val Val Ser Ser Cys Gly His Asp Gly Pro Phe Gly Ala Thr Gly Val
225                 230                 235                 240

Lys Arg Leu Lys Ser Ile Gly Leu Ile Asp Ser Val Pro Gly Met Lys
                245                 250                 255

Ala Leu Asp Met Asn Lys Ala Glu Asp Ala Ile Val Arg Leu Thr Arg
            260                 265                 270

Glu Val Val Pro Gly Met Ile Val Thr Gly Met Glu Val Ala Glu Ile
        275                 280                 285

Asp Gly Ala Pro Arg Met Gly Pro Thr Phe Gly Ala Met Met Ile Ser
    290                 295                 300

Gly Gln Lys Ala Ala His Leu Ala Leu Arg Ser Leu Gly Leu Pro Asn
305                 310                 315                 320

Ala Leu Asp Ser Val Gly Asn Val His Pro Glu Leu Val Leu Ala Ala
                325                 330                 335

Ala Glu Ser Ala Glu Ile Ala Glu Ala
            340                 345

<210> SEQ ID NO 45
<211> LENGTH: 345
<212> TYPE: PRT
<213> ORGANISM: Glycine max

<400> SEQUENCE: 45

Met Ala Ser Ser Thr Ile Thr Ser Ser Phe Leu Thr Ser Pro Pro Ser
1               5                   10                  15

Ser Leu Phe Asn Lys Ser Ser Pro Ser Phe His Ala Thr Pro Thr
            20                  25                  30

Leu Arg Pro Leu Ala Pro Arg Ala Ser Met Ser Ala Ser Ala Pro Pro
        35                  40                  45

Tyr Asp Phe Gly Ser Phe Arg Phe Asp Pro Ile Arg Glu Ser Ile Val
    50                  55                  60

Ser Arg Glu Met Thr Arg Arg Tyr Met Ile Asp Met Val Thr His Ala
65                  70                  75                  80

Asp Thr Asp Val Val Ile Val Gly Ala Gly Ser Ala Gly Leu Ser Cys
                85                  90                  95

Ala Tyr Glu Leu Ser Lys Asn Pro Ser Ile Asn Ile Ala Ile Val Glu
            100                 105                 110

Gln Ser Val Ser Pro Gly Gly Gly Ala Trp Leu Gly Gly Gln Leu Phe
```

-continued

```
                115                 120                 125
Ser Ala Met Val Val Arg Lys Pro Ala His Leu Phe Leu Asp Glu Leu
    130                 135                 140

Asn Val Glu Tyr Asp Glu Gln Asp Asn Tyr Val Val Ile Lys His Ala
145                 150                 155                 160

Ala Leu Phe Thr Ser Thr Ile Met Ser Lys Leu Leu Ala Arg Pro Asn
                165                 170                 175

Val Lys Leu Phe Asn Ala Val Ala Ala Glu Asp Leu Ile Val Lys Asn
                180                 185                 190

Gly Arg Val Gly Gly Val Val Thr Asn Trp Ala Leu Val Ser Leu Asn
                195                 200                 205

His Asp Thr Gln Ser Cys Met Asp Pro Asn Val Met Glu Ala Lys Val
    210                 215                 220

Val Val Ser Ser Cys Gly His Asp Gly Pro Phe Gly Ala Thr Gly Val
225                 230                 235                 240

Lys Arg Leu Lys Ser Ile Gly Leu Ile Asp Ser Val Pro Gly Met Lys
                245                 250                 255

Ala Leu Asp Met Asn Lys Ala Glu Asp Ala Ile Val Arg Leu Thr Arg
                260                 265                 270

Glu Val Val Pro Gly Met Ile Val Thr Gly Met Glu Val Ala Glu Ile
                275                 280                 285

Asp Gly Ala Pro Arg Met Gly Pro Thr Phe Gly Ala Met Met Ile Ser
    290                 295                 300

Gly Gln Lys Ala Ala His Leu Ala Leu Arg Ser Leu Gly Leu Pro Asn
305                 310                 315                 320

Ala Leu Asp Ser Val Gly Asn Val His Pro Glu Leu Val Leu Ala Ala
                325                 330                 335

Ala Glu Ser Ala Glu Ile Ala Glu Ala
                340                 345
```

THIAMINE BIOSYNTHETIC ENZYMES

This application claims priority benefit of U.S. Provisional Application No. 60/139,556 filed Jun. 16, 1999.

FIELD OF THE INVENTION

This invention is in the field of plant molecular biology. More specifically, this invention pertains to nucleic acid fragments encoding thiamine biosynthetic enzymes in plants and seeds.

BACKGROUND OF THE INVENTION

Many vertebrates, including man, lack the ability to manufacture certain essential cofactors and therefore these cofactors must be made available and therefore must be present in their diet. These cofactors are vitamins. Plants serve as the ultimate source of vitamins for humans and animals, thus, the ability to manipulate the production and accumulation of vitamins in plants would be of considerable importance and value. Furthermore, the inability of humans and animals to synthesize these cofactors provides a useful distinction between human or animal and plant cellular metabolism. This distinction can be exploited for the discovery of herbicidal chemical compounds that target enzymes in the plant biosynthetic pathways of vitamins while having a low toxicity to animals.

Thiamine, or vitamin B1, is a cofactor for transketolase, pyruvate dehydrogenase and alpha-ketoglutarate dehydrogenase. The biosynthetic pathway for thiamine production has been extensively studied in yeasts and bacteria but little plant data is available. The *E. coli* thiamine biosynthetic enzyme C (thiC) has a predicted molecular weight of 70 kDa (Vander Horn et al. (1993) *J. Bacteriol.* 175:982–992). The *B. subtilis* thiamine biosynthetic enzyme C has thiamine phosphate synthase activity converting thiazole phosphate and pyrimidine pyrophosphate to thiamine (Zhang et al. (1997) *J. Bacteriol.* 179:3030–3035). The THI4 gene from *S. cerevisiae* is induced upon the depletion of thiamine and appears to play a role in mitochondrial DNA damage control (Machado et al. (1997) *J. Mol. Biol.* 273:114–121). Genes encoding two corn thiamine biosynthetic enzymes (thi1-1 and thi1-2) which complement the yeast thi4 mutant have been identified. These cDNAs have very little similarity at their 3' untranslated regions. The polypeptides encoded by these genes are involved in the production of thiazole, a thiamine precursor, have a conserved central region and more variable amino- and carboxy- terminii. Both polypeptides contain signal sequences which resemble plastid transit peptides (Belanger et al. (1995) *Plant Mol. Biol.* 29:809–821).

Identification of the genes encoding thi1-1, thi1-2, and thiC will allow the manipulation of vitamin B1 production in crop plants and thereby allowing for the improvement of their nutritional value. Manipulation of these enzymes may affect the achievable levels of xanthophylls in corn endosperm. Finally, these enzymes are involved in the production of plastid-derived isoprenoids, and as such are good herbicide targets.

SUMMARY OF THE INVENTION

The present invention concerns an isolated polynucleotide comprising a nucleotide sequence selected from the group consisting of: (a) first a nucleotide sequence comprising at least 450 nucleotides selected from SEQ ID NOs:1, 3, 5, 7, 9, 11, 13, 15, 17, 19, 21, 23, 25, 27, 29, 31, 33, 35, 37, and 43; (b) a second nucleotide sequence encoding a polypeptide of at least 90 amino acids having at least 97% identity based on the Clustal method of alignment when compared to a polypeptide selected from the group consisting of SEQ ID NOs:2, 4, 6, 8, 10, 12, 14, 16, 18, 20, 22, 24, 26, 28, 30, 32, 34, 36, 38, and 44; and (c) a third nucleotide sequence comprising the complement of (a) or (b).

In a second embodiment, this invention relates to a chimeric gene comprising an isolated polynucleotide of the present invention operably linked to at least one suitable regulatory sequence.

In a third embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a fourth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a fifth embodiment, the invention concerns a thi or a thiC polypeptide of at least 90 amino acids comprising at least 97% identity based on the Clustal method of alignment when compared to a polypeptide selected from the group consisting of SEQ ID NOs:2, 4, 6, 8, 10, 12, 14, 16, 18, 20, 22, 24, 26, 28, 30, 32, 34, 36, 38, and 44.

In a sixth embodiment, the invention relates to a method of selecting an isolated polynucleotide that affects the level of expression of a thi1 or a thiC polypeptide or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the thi1 or the thiC polypeptide or enzyme activity in the host cell containing the isolated polynucleotide; and (d) comparing the level of the thi1 or the thiC polypeptide or enzyme activity in the host cell containing the isolated polynucleotide with the level of the thi or the thiC polypeptide or enzyme activity in the host cell that does not contain the isolated polynucleotide.

In a seventh embodiment, the invention concerns a method of obtaining a nucleic acid fragment encoding a substantial portion of a thi1 or a thiC polypeptide, preferably a plant thi1 or thiC polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, and 43, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a thi1 or a thiC amino acid sequence.

In an eighth embodiment, this invention relates to a method of obtaining a nucleic acid fragment encoding all or a substantial portion of the amino acid sequence encoding a thi1 or a thiC polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a ninth embodiment, this invention concerns a composition, such as a hybridization mixture, comprising an isolated polynucleotide or an isolated polypeptide of the present invention.

In a tenth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the thi1 or the thiC polynucleotide in an amount sufficient to complement a null mutant to provide a positive selection means.

In an eleventh embodiment, this invention relates to a method of altering the level of expression of a thiamine biosynthetic enzyme in a host cell comprising: (a) transforming a host cell with a chimeric gene of the present invention; and (b) growing the transformed host cell under conditions that are suitable for expression of the chimeric gene wherein expression of the chimeric gene results in production of altered levels of the thiamine biosynthetic enzyme in the transformed host cell.

In a twelfth embodiment, this invention concerns an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37, and the complement of such sequences.

A further embodiment of the instant invention is a method for evaluating at least one compound for its ability to inhibit the activity of a thiamine biosynthetic enzyme, the method comprising the steps of: (a) transforming a host cell with a chimeric gene comprising a nucleic acid fragment encoding the thiamine biosynthetic enzyme, operably linked to at least one suitable regulatory sequence; (b) growing the transformed host cell under conditions that are suitable for expression of the chimeric gene wherein expression of the chimeric gene results in production of the thiamine biosynthetic enzyme in the transformed host cell; (c) optionally purifying the thiamine biosynthetic enzyme expressed by the transformed host cell; (d) treating the thiamine biosynthetic enzyme with a compound to be tested; and (e) comparing the activity of the thiamine biosynthetic enzyme that has been treated with a test compound to the activity of an untreated thiamine biosynthetic enzyme, thereby selecting compounds with potential for inhibitory activity.

BRIEF DESCRIPTION OF THE DRAWINGS AND SEQUENCE LISTINGS

The invention can be more fully understood from the following detailed description, the accompanying drawings and Sequence Listing which form a part of this application.

FIGS. 1(1A–1C) presents an alignment of the thi1 amino acid sequences derived from rice clone rlr6.pk0083.f11:fis (SEQ ID NO:22), soybean clone sah1c.pk004.b24:fis (SEQ ID NO:24), and wheat clones wlm1.pk0018.b5:fis (SEQ ID NO:26) and wdk3c.pk006.c16:fis (SEQ ID NO:30) with the *Zea mays* thi1-1 (NCBI General Identifier No. 2501189; SEQ ID NO:39) and thi1-2 sequences (NCBI General Identifier No. 2501190; SEQ ID NO:40). Amino acids conserved among all the sequences are indicated by an asterisk (*) above the alignment. Dashes are used by the program to maximize the alignment.

FIGS. 2(2A–2C) presents an alignment of the thiC amino acid sequences derived from corn clone p0018.chstg60r:fis (SEQ ID NO:32) and wheat clone wkm2c.pk005.e4:fis (SEQ ID NO:38) with the Arabidopsis thaliana (NCBI General Identifier No. 3582335; SEQ ID NO:42) and *Bacillus subtilis* thiC sequences (NCBI General Identifier No. 3041750; SEQ ID NO:41). Amino acids conserved among all the sequences are indicated by an asterisk (*) above the alignment while those conserved only among plant sequences are indicated by a plus sign (+) above the alignment. Dashes are used by the program to maximize the alignment.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Thiamine Biosynthetic Enzymes

| Protein | Clone Designation | SEQ ID NO: (Nucleotide) | SEQ ID NO: (Amino Acid) |
|---|---|---|---|
| Rice thi1 | rlr6.pk0083.f11 | 1 | 2 |
| Soybean thi1 | sah1c.pk004.b24 | 3 | 4 |
| Wheat thi1 | wlm1.pk0018.b5 | 5 | 6 |
| Rice thi1 | rlr72.pk0006.cl | 7 | 8 |
| Soybean thi1 | scr1c.pk004.n23 | 9 | 10 |
| Wheat thi1 | wdk3c.pk006.c16 | 11 | 12 |
| Corn thiC | p0018.chstg60r | 13 | 14 |
| Rice thiC | rls6.pk0079.a6 | 15 | 16 |
| Soybean thiC | se1.pk0035.e2 | 17 | 18 |
| Wheat thiC | wkm2c.pk005.e4 | 19 | 20 |
| Rice thi1 | rlr6.pk0083.f11:fis | 21 | 22 |
| Soybean thi1 | sahlc.pk004.b24:fis | 23 | 24 |
| Wheat thi1 | wlm1.pk0018.b5:fis | 25 | 26 |
| Rice thi1 | rlr72.pk0006.c1:fis | 27 | 28 |
| Wheat thi1 | wdk3c.pk006.c16:fis | 29 | 30 |
| Corn thiC | p0018.chstg60r:fis | 31 | 32 |
| Rice thiC | rls6.pk0079.a6:fis | 33 | 34 |
| Soybean thiC | se1.pk0035.e2:fis | 35 | 36 |
| Wheat thiC | wkm2c.pk005.e4:fis | 37 | 38 |
| Soybean thi1 | scr1c.pk004.n23:fis | 43 | 44 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment" "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NOs:1, 3, 5, 7, 9, 11, 13, 15, 17, 19, 21, 23, 25, 27, 29, 31, 33, 35, 37, and 43, or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through, for example, antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modification is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, and 43, and the complement of such nucleotide sequences may be used in methods of selecting an isolated polynucleotide that affects the expression of a thiamine biosynthetic enzyme in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS which was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computerbased sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon bias" exhibited by a specific host cell in the usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function. "Altered levels" or "altered expression" refer to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277)

and particle-accelerated or "gene gun" transformation technology (Klein et al. (1987) *Nature (London)* 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence of at least 450 nucleotides selected from SEQ ID NOs:1, 3, 5, 7, 9, 11, 13, 15, 17, 19, 21, 23, 25, 27, 29, 31, 33, 35, 37, and 43; (b) a second nucleotide sequence encoding a polypeptide of at least 90 amino acids having at least 97% identity based on the Clustal method of alignment when compared to a polypeptide selected from the group consisting of SEQ ID NOs:2, 4, 6, 8, 10, 12, 14, 16, 18, 20, 22, 24, 26, 28, 30, 32, 34, 36, 38, and 44; and (c) a third nucleotide sequence comprising the complement of (a) or (b).

Nucleic acid fragments encoding at least a substantial portion of several thiamine biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other thi or thiC, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, and 43 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a thiamine biosynthetic enzyme, preferably a substantial portion of a plant thi1 or thiC, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, and 43, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a thi1 or a thiC enzyme.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of thiamine in those cells. Thiamine pyrophosphate is a co-factor in transketolase enzymes such as 1-deoxy-D-xylulose-5-phosphate synthase, a key enzyme in the biosynthesis of plastid-derived isoprenoids. The thiamine biosynthetic enzymes are good herbicide targets because isoprenoids are essential for growth, development, and defense in plants. Xanthophylls are isoprenoids which have value as coloring agents in poultry feeds. Manipulation of the thiamine biosynthetic enzymes in transgenic plants may affect the achievable levels of xanthophyls in those plants. Manipulation of thi1 and/or thiC may also increase the amount of vitamin B in the cell improving the nutritional value of the plant.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 90 amino acids that has at least 97% identity based on the Clustal method of alignment when compared to a polypeptide selected from the group consisting of SEQ ID NOs:2, 4, 6, 8, 10, 12, 14, 16, 18, 20, 22, 24, 26, 28, 30, 32, 34, 36, 38, and 44.

The instant polypeptides (or substantial portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded thiamine biosynthetic enzyme. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in thiamine biosynthesis. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allelespecific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
| --- | --- | --- |
| p0018 | Corn Seedling After 10 Day Drought, Heat Shocked for 24 Hours, Harvested After Recovery at Normal Growth Conditions for 8 Hours | p0018.chstg60r |
| rlr6 | Rice Leaf 15 Days After Germination, 6 Hours After Infection of Strain *Magaporthe grisea* 4360-R-62 (AVR2-YAMO); Resistant | rlr6.pk0083.fl1 |
| rlr72 | Rice Leaf 15 Days After Germination, 72 Hours After Infection of Strain *Magaporthe grisea* 4360-R-62 (AVR2-YAMO); Resistant | rlr72.pk0006.cl |
| rls6 | Rice Leaf 15 Days After Germination, 6 Hours After Infection of Strain *Magaporthe grisea* 4360-R-67 (AVR2-YAMO); Susceptible | rls6.pk0079.a6 |
| sah1c | Soybean Sprayed With Authority Herbicide | sah1c.pk004.b24 |
| scr1c | Soybean Embryogenic Suspension Culture Subjected to 4 Vacuum Cycles and Collected 12 Hours Later | scr1c.pk004.n23 |
| se1 | Soybean Embryo, 6 to 10 Days After Flowering | se1.pk0035.e2 |
| wdk3c | Wheat Developing Kernel, 14 Days After Anthesis | wdk3c.pk006.c16 |
| wkm2c | Wheat Kernel Malted 175 Hours at 4 Degrees Celsius | wkm2c.pk005.e4 |
| wlm1 | Wheat Seedlings 1 Hour After Inoculation With *Erysiphe graminis f.* sp *tritici* | wlm1.pk0018.b5 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding thiamine biosynthetic enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Thiamine Biosynthetic Enzyme 1 (thi1)

The BLASTX search using the EST sequences from clones listed in Table 3 revealed similarity of the polypeptides encoded by the cDNAs to thi1-1 and thi1-2 from *Zea mays* (NCBI General Identifier No. 2501189 and 2501190, respectively). Shown in Table 3 are the BLAST results for individual ESTs ("EST"):

TABLE 3

BLAST Results for Sequences Encoding Polypeptides Homologous to Thiamine Biosynthetic Enzyme 1 (thi1)

| | | BLAST pLog Score | |
| --- | --- | --- | --- |
| Clone | Status | 2501189 (*Zea mays*) | 2501190 (*Zea mays*) |
| rlr6.pk0083.fl1 | EST | 58.30 | 53.70 |
| sah1c.pk004.b24 | EST | 48.70 | 47.00 |
| wlm1.pk0018.b5 | EST | 58.00 | 57.30 |
| rlr72.pk0006.c1 | EST | 62.05 | 62.70 |
| scr1c.pk004.n23 | EST | 39.70 | 40.40 |
| wdk3c.pk006.c16 | EST | 70.22 | 71.30 |

The sequence of the entire cDNA insert in clones rlr6.pk0083.f11, sah1c.pk004.b24, wlm1.pk0018.b5, rlr72.pk0006.c1scr1c.pk004.n23, and wdk3c.pk006.c16 was determined. The BLASTP search using the amino acid sequence encoded by the clone scr1c.pk004.n23:fis revealed similarity of the polypeptides encoded by the cDNA to thiamine biosynthetic enzyme from *Glycine max* (NCBI General Identifier No. 6552395) with a pLog value of >254.00. The BLASTP search using the amino acid sequences encoded by clones listed in Table 4 revealed similarity of the polypeptides encoded by the cDNAs to thi1-1 from *Zea mays* and *Citrus sinensis* (NCBI General Identifier Nos. 2501189 and 6094476, respectively) and to thi1-2 from *Zea mays* (NCBI General Identifier No. 2501190). Shown in Table 4 are the BLAST results for the amino acid sequences derived from the sequences of the entire cDNA inserts comprising the indicated cDNA clones ("FIS"), or for the amino acid sequences derived from FISs encoding entire thi1s ("CGS"):

GENE bioinformatics computing suite (DNASTAR Inc., Madison, Wis.) Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode substantial portions and an entire rice thi polypeptide, a substantial portion and one entire soybean

TABLE 4

BLAST Results for Sequences Encoding Polypeptides Homologous to Thiamine Biosynthetic Enzyme 1 (thi1)

| | | BLAST pLog Score | | |
|---|---|---|---|---|
| Clone | Status | 2501189 (*Zea mays*) | 6094476 (*Citrus sinensis*) | 2501190 (*Zea mays*) |
| rlr6.pk0083.fl1:fis | CGS | 166.00 | 153.00 | 165.00 |
| sah1c.pk004.b24:fis | CGS | 150.00 | 150.00 | 149.00 |
| wlm1.pk0018.b5:fis | CGS | 460.00 | 152.00 | 164.00 |
| rlr72.pk0006.c1:fis | FIS | 55.40 | 53.70 | 56.52 |
| wdk3c.pk006.c16:fis | CGS | 120.00 | 116.00 | 122.00 |

FIG. 1 presents an alignment of the amino acid sequences set forth in SEQ ID NOs:22, 23, 26, and 30 and the *Zea mays* thi1-1 and thi1-2 sequences (SEQ ID NO:39 and respectively). The data in Table 5 presents a calculation of the percent amino acid sequences set forth in SEQ ID NOs:2, 4, 6, 8, 10, 12, 22, 24, 26, 28, and 30 and the *Zea mays* thi1-1sequence (NCBI General Identifier No. 2501189;SEQ ID NO:39), the *Zea mays* thi1-2 sequence (NCBI General Identifier No. 2501189; SEQ ID NO:40) and *Citrus sinensis* thi1 sequence (NCBI General Identifier No. 6094476).

TABLE 5

Percent Identity of Amino Acid Sequences Deduced From the Nucleotide Sequences of cDNA Clones Encoding Polypeptides Homologous to Thiamine Biosynthetic Enzyme 1 (thi1)

| | Percent Identity to | | |
|---|---|---|---|
| SEQ ID NO. | 2501189 (*Zea mays*) | 2501190 (*Zea mays*) | 6094476 (*Citrus sinensis*) |
| 2 | 86.7 | 81.9 | 80.0 |
| 4 | 88.1 | 85.1 | 82.2 |
| 6 | 85.7 | 83.8 | 81.0 |
| 8 | 81.7 | 82.5 | 77.8 |
| 10 | 63.7 | 66.4 | 61.9 |
| 12 | 75.3 | 76.0 | 71.2 |
| 22 | 81.9 | 80.8 | 75.5 |
| 24 | 76.6 | 76.6 | 77.2 |
| 26 | 80.1 | 80.9 | 76.4 |
| 28 | 77.2 | 77.9 | 75.0 |
| 30 | 67.8 | 67.5 | 64.4 |

FIG. 3 presents an alignment of the amino acid sequences set forth in SEQ ID NO:44 and the *Glycine max* thiamine biosynthetic enzyme sequence (SEQ ID NO:45). The amino acid sequence set forth in SEQ ID NO:44 is 96.5% identical to the *Glycine max* sequence (NCBI General Identifier No. 6552395, SEQ ID NO:45).

Sequence alignments and percent identity calculations were performed using the Megalign program of the LASERthi polypeptide, and substantial portions and three entire soybean thi1 polypeptides.

Example 4

Characterization of cDNA Clones Encoding Thiamine Biosynthetic Enzyme C (thiC)

The BLASTX search using the EST sequences from clones listed in Table 6 revealed similarity of the polypeptides encoded by the cDNAs to thiamine biosynthetic enzyme C from *Bacillus subtilis, Escherichia coli* or *Mycobacterium tuberculosis* (NCBI General Identifier Nos. 3041750, 421172, 417994 and 3024726, respectively). Shown in Table 6 are the BLAST results for individual ESTs ("EST"):

TABLE 6

BLAST Results for Sequences Encoding Polypeptides Homologous to Thiamine Biosynthetic Enzyme C

| Clone | Status | Organism | NCBI GI No. | BLAST pLog Score |
|---|---|---|---|---|
| p0018.chstg60r | EST | *B. subtilis* | 3041750 | 40.40 |
| rls6.pk0079.a6 | EST | *E. Coli* | 421172 | 60.00 |
| se1.pk0035.e2 | EST | *E. Coli* | 417994 | 63.05 |
| wkm2c.pk005.e4 | EST | *M. tuberculosis* | 3024726 | 20.70 |

The sequence of the entire cDNA insert of the clones listed in Table 6 was determined. The BLASTP search using the amino acid sequences derived from clones listed in Table 7 revealed similarity of the polypeptides encoded by the contig to putative thiamin biosynthesis protein from *Arabidopsis thaliana* (NCBI General Identifier No. 3582335) and by the.cDNAs to thiC from *Bacillus subtilis* (NCBI General Identifier No. 3041750). Shown in Table 7 are the BLAST results for the amino acid sequences derived from the sequences of the entire cDNA inserts comprising the indicated cDNA clones ("FIS"), or for the amino acid sequences derived from FISs encoding entire thiCs ("CGS"):

TABLE 7

BLAST Results for Sequences Encoding Polypeptides Homologous to Thiamine Biosynthetic Enzyme C

| | | BLAST pLog Score | |
|---|---|---|---|
| Clone | Status | 3041750 (*Bacillus subtilis*) | 3582335 (*Arabidopsis thaliana*) |
| p0018.chstg60r:fis | CGS | >254.00 | >254.00 |
| rls6.pk0079.a6:fis | FIS | 149.00 | >254.00 |
| se1.pk0035.e2:fis | FIS | 136.00 | >254.00 |
| wkm2c.pk005.e4:fis | CGS | >254.00 | >254.00 |

FIG. 2 presents an alignment of the amino acid sequences set forth in SEQ ID NOs:32 and 38 and the *Arabidopsis thaliana* (NCBI General Identifier No. 3582335; SEQ ID NO:42) and *Bacillus subtilis* sequences (NCBI General Identifier No. 3041750; SEQ ID NO:41). The data in Table 8 presents a calculation of the percent identity of the amino acid sequences set forth in SEQ ID NOs:14, 16, 18, 20, 32, 34, 36, and 38 with the *Arabidopsis thaliana* and the *Bacillus subtilis* sequences (SEQ ID NO:41 and SEQ ID NO:42, respectively).

TABLE 8

Percent Identity of Amino Acid Sequences Deduced From the Nucleotide Sequences of cDNA Clones Encoding Polypeptides Homologous to thiC

| | Percent Identity to | |
|---|---|---|
| SEQ ID NO. | 3041750 (*Bacillus subtilis*) | 3582335 (*Arabidopsis thaliana*) |
| 14 | 72.4 | 87.9 |
| 16 | 72.3 | 81.0 |
| 18 | 77.2 | 90.1 |
| 20 | 37.5 | 86.9 |
| 32 | 63.1 | 87.8 |
| 34 | 61.0 | 91.5 |
| 36 | 67.3 | 96.1 |
| 38 | 58.4 | 82.4 |

Sequence alignments and percent identity calculations were performed using the Megalign program of the LASER-GENE bioinformatics computing suite (DNASTAR Inc., Madison Wis.) Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode a substantial portion and an entire or almost entire corn, rice, soybean, and wheat thiC.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of mercury (Hg). The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches of mercury (Hg). The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC Corp., Philadelphia, Pa.). Buffer and agarose contain 10 µg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Thiamine Biosynthetic Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for thiamine biosynthetic enzyme 1 are presented by Belanger et al. (1995) *Plant Mol. Biol.* 29:809–821. Assays for thiamine biosynthetic enzyme C are presented by Zhang et al. (1997) *J. Bacteriol.* 179:3030–3035.

What is claimed is:

1. An isolated polynucleotide comprising:
   (a) a nucleotide sequence encoding a polypeptide having thiamine biosynthetic enzyme 1 activity, wherein the amino acid sequence of the polypeptide and the amino acid sequence of SEQ ID NO:24 have at least 80% sequence identity based on the Clustal alignment method, or
   (b) the complement of said nucleotide sequence, wherein the complement and the nucleotide sequence contain the same number of nucleotides and are 100% complementary.

2. The polynucleotide of claim 1 wherein the sequence identity is at least 85% based on the Clustal alignment method.

3. The polynucleotide of claim 1 wherein the sequence identity is at least 90% based on the Clustal alignment method.

4. The polynucleotide of claim 1 wherein the sequence identity is at least 95% based on the Clustal alignment method.

5. The polynucleotide of claim 1 wherein the polynucleotide encodes the polypeptide sequence of SEQ ID NO:24.

6. The polynucleotide of claim 1 wherein said nucleotide sequence comprises the nucleotide sequence of SEQ ID NO:23.

7. A vector comprising the polynucleotide of claim 1.

8. A recombinant DNA construct comprising the polynucleotide of claim 1 operably linked to at least one regulatory sequence.

9. A cell comprising the recombinant DNA construct of claim 8.

10. The cell of claim 9 wherein said cell is a plant cell or a bacterial cell.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

14. A method for transforming a cell, comprising introducing into a cell the polynucleotide of claim 1.

* * * * *